US012035971B2

(12) United States Patent
Abramoff et al.

(10) Patent No.: US 12,035,971 B2
(45) Date of Patent: *Jul. 16, 2024

(54) AUTOMATED DETERMINATION OF ARTERIOVENOUS RATIO IN IMAGES OF BLOOD VESSELS

(71) Applicants: University of Iowa Research Foundation, Iowa City, IA (US); United States Government as Represented by the Department of Veterans Affairs, Washington, DC (US)

(72) Inventors: Michael D. Abramoff, University Heights, IA (US); Meindert Niemeijer, Iowa City, IA (US); Xiayu Xu, Iowa City, IA (US); Milan Sonka, Coralville, IA (US); Joseph M. Reinhardt, Iowa City, IA (US)

(73) Assignees: University of Iowa Research Foundation, Iowa City, IA (US); United States Government as Represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/185,704

(22) Filed: Mar. 17, 2023

(65) Prior Publication Data
US 2023/0255478 A1 Aug. 17, 2023

Related U.S. Application Data

(63) Continuation of application No. 15/936,162, filed on Mar. 26, 2018, now Pat. No. 11,638,522, which is a
(Continued)

(51) Int. Cl.
*A61B 3/12* (2006.01)
*A61B 3/00* (2006.01)

(52) U.S. Cl.
CPC .............. *A61B 3/12* (2013.01); *A61B 3/0016* (2013.01); *A61B 3/0058* (2013.01); *A61B 3/1225* (2013.01)

(58) Field of Classification Search
CPC ....... A61B 3/12; A61B 3/1241; A61B 3/1233; A61B 3/1225
(Continued)

(56) References Cited

U.S. PATENT DOCUMENTS 4,883,061 A 11/1989 Zeimer
4,998,533 A 3/1991 Winkelman
(Continued)

FOREIGN PATENT DOCUMENTS

AU 2012207076 7/2012
CA 2610345 12/2006
(Continued)

OTHER PUBLICATIONS

Abramoff, M. et al., Image Processing with Image. J Biophotonics Int. 2004; 11(7):36-42.
(Continued)

*Primary Examiner* — Zachary W Wilkes
(74) *Attorney, Agent, or Firm* — Ballard Spahr LLP

(57) ABSTRACT

The methods and systems provided can automatically determine an Arteriolar-to-Venular diameter Ratio, AVR, in blood vessels, such as retinal blood vessels and other blood vessels in vertebrates. The AVR is an important predictor of increases in the risk for stroke, cerebral atrophy, cognitive decline, and myocardial infarct.

20 Claims, 15 Drawing Sheets

Related U.S. Application Data continuation of application No. 13/355,386, filed on Jan. 20, 2012, now Pat. No. 9,924,867.

(60) Provisional application No. 61/434,551, filed on Jan. 20, 2011.

(58) Field of Classification Search
USPC .................................................. 351/206, 246
See application file for complete search history.

(56) References Cited

U.S. PATENT DOCUMENTS

| | | |
|---|---|---|
| 5,233,517 A | 8/1993 | Jindra |
| 5,270,924 A | 12/1993 | Hideshima |
| 5,303,709 A | 4/1994 | Dreher et al. |
| 5,857,030 A | 1/1999 | Gaborski et al. |
| 5,868,134 A | 2/1999 | Sugiyama et al. |
| 6,000,799 A | 12/1999 | Van de Velde |
| 6,003,993 A | 12/1999 | Webb |
| 6,044,181 A | 3/2000 | Szeliski et al. |
| 6,053,865 A | 4/2000 | Sugiyama et al. |
| 6,104,828 A | 8/2000 | Shioiri |
| 6,179,421 B1 | 1/2001 | Pang |
| 6,276,798 B1 | 8/2001 | Gil et al. |
| 6,453,057 B1 | 9/2002 | Marshall et al. |
| 6,556,853 B1 | 4/2003 | Cabib et al. |
| 6,567,682 B1 | 5/2003 | Osterweil et al. |
| 6,674,894 B1 | 1/2004 | Parker et al. |
| 6,712,469 B2 | 3/2004 | Ando |
| 6,714,672 B1 | 3/2004 | Berestov et al. |
| 6,728,561 B2 | 4/2004 | Smith et al. |
| 6,731,782 B2 | 5/2004 | Ashton |
| 6,757,409 B2 | 6/2004 | Marshall et al. |
| 6,830,336 B2 | 12/2004 | Fransen |
| 6,845,260 B2 | 1/2005 | Liu et al. |
| 6,996,260 B1 | 2/2006 | Skands et al. |
| 7,104,958 B2 | 9/2006 | Crutchfield et al. |
| 7,206,435 B2 | 4/2007 | Fujimura et al. |
| 7,232,240 B2 | 6/2007 | Kosnik et al. |
| 7,242,810 B2 | 7/2007 | Chang |
| 7,343,032 B2 | 3/2008 | Oakley et al. |
| 7,474,775 B2 | 1/2009 | Abramoff et al. |
| 7,524,061 B2 | 4/2009 | Yan et al. |
| 7,574,028 B2 | 8/2009 | Luo et al. |
| 7,578,028 B2 | 8/2009 | Sellars |
| 7,620,501 B2 | 11/2009 | Tek et al. |
| 7,712,898 B2 | 5/2010 | Abramoff et al. |
| 7,715,597 B2 | 5/2010 | Costache et al. |
| 8,140,329 B2 | 3/2012 | Zhang et al. |
| 8,180,134 B2 | 5/2012 | Wang |
| 8,194,936 B2 | 6/2012 | Abramoff et al. |
| 8,340,437 B2 | 12/2012 | Abramoff et al. |
| 8,463,065 B2 | 6/2013 | Sun et al. |
| 8,611,623 B2 | 12/2013 | Kurihara et al. |
| 8,616,702 B2 | 12/2013 | Abramoff |
| 8,634,628 B2 | 1/2014 | Inoue |
| 8,639,002 B2 | 1/2014 | Tanaka et al. |
| 8,687,862 B2 | 4/2014 | Hsu |
| 8,761,473 B2 | 6/2014 | Ihara |
| 8,842,894 B2 | 9/2014 | Ihara |
| 9,307,926 B2 | 4/2016 | Begin et al. |
| 9,355,458 B2 | 5/2016 | Ihara |
| 9,679,389 B2 | 6/2017 | Ostrovsky-Berman et al. |
| 9,924,867 B2 | 3/2018 | Abramoff |
| 2002/0024516 A1 | 2/2002 | Chen et al. |
| 2002/0126915 A1 | 9/2002 | Lai et al. |
| 2002/0165837 A1 | 11/2002 | Zhang et al. |
| 2003/0071970 A1 | 4/2003 | Donnerhacke et al. |
| 2003/0166999 A1 | 9/2003 | Liu et al. |
| 2003/0215119 A1 | 11/2003 | Uppaluri et al. |
| 2004/0032488 A1 | 2/2004 | Harman |
| 2004/0037453 A1 | 2/2004 | Marshall et al. |
| 2004/0064057 A1 | 4/2004 | Siegel |
| 2004/0085542 A1 | 5/2004 | Soliz et al. |
| 2004/0105074 A1 | 6/2004 | Soliz et al. |
| 2006/0023990 A1 | 2/2006 | Shih et al. |
| 2006/0056727 A1 | 3/2006 | Jones et al. |
| 2006/0119858 A1 | 6/2006 | Knighton et al. |
| 2006/0140446 A1 | 6/2006 | Luo et al. |
| 2007/0002275 A1 | 1/2007 | Yan et al. |
| 2007/0020795 A1 | 1/2007 | Mori et al. |
| 2007/0058865 A1 | 3/2007 | Li et al. |
| 2007/0083492 A1 | 4/2007 | Hohimer et al. |
| 2007/0092864 A1 | 4/2007 | Reinhardt et al. |
| 2007/0110298 A1 | 5/2007 | Graepel et al. |
| 2007/0122007 A1 | 5/2007 | Austin et al. |
| 2007/0183661 A1 | 8/2007 | El-Maleh et al. |
| 2007/0230795 A1 | 10/2007 | Abramoff et al. |
| 2007/0244396 A1 | 10/2007 | Vilser et al. |
| 2007/0253171 A1 | 11/2007 | Cheng et al. |
| 2008/0205717 A1 | 8/2008 | Reeves et al. |
| 2008/0240547 A1 | 10/2008 | Cho et al. |
| 2008/0309881 A1 | 12/2008 | Huang et al. |
| 2009/0148024 A1 | 6/2009 | Park |
| 2009/0257024 A1 | 10/2009 | Luther et al. |
| 2010/0002929 A1 | 1/2010 | Sammak et al. |
| 2010/0034457 A1 | 2/2010 | Berliner et al. |
| 2010/0061601 A1 | 3/2010 | Abramoff et al. |
| 2010/0074532 A1 | 3/2010 | Gordon et al. |
| 2010/0082692 A1 | 4/2010 | Akinyemi et al. |
| 2010/0103249 A1 | 4/2010 | Lipton et al. |
| 2010/0104150 A1 | 4/2010 | Saint Felix et al. |
| 2010/0118161 A1 | 5/2010 | Tsurumi |
| 2010/0142824 A1 | 6/2010 | Lu |
| 2010/0177943 A1 | 7/2010 | Zhao et al. |
| 2010/0182406 A1 | 7/2010 | Benitez |
| 2010/0271511 A1 | 10/2010 | Ma et al. |
| 2010/0284180 A1 | 11/2010 | Popovich et al. |
| 2011/0026794 A1 | 2/2011 | Sundar et al. |
| 2011/0134221 A1 | 6/2011 | Lee et al. |
| 2011/0135172 A1 | 6/2011 | Kitamura |
| 2012/0236259 A1 | 9/2012 | Abramoff et al. |
| 2012/0237094 A1 | 9/2012 | Kurihara et al. |
| 2013/0208960 A1 | 8/2013 | Reisman |
| 2014/0035901 A1 | 2/2014 | Chen et al. |
| 2015/0379708 A1 | 12/2015 | Abramoff et al. |

FOREIGN PATENT DOCUMENTS

| | | |
|---|---|---|
| CA | 2825169 | 7/2012 |
| EP | 0905509 A1 | 3/1999 |
| EP | 2665406 | 7/2012 |
| JP | 2007-097634 A | 4/2007 |
| JP | 2010-500081 A | 1/2010 |
| JP | 60-05663 B2 | 10/2016 |
| WO | WO-89/05493 | 6/1989 |
| WO | WO-2005/076198 | 8/2005 |
| WO | WO-2006/023990 A2 | 3/2006 |
| WO | WO-2006/105473 | 10/2006 |
| WO | WO-2007/031818 | 3/2007 |
| WO | WO-2007/118079 | 10/2007 |
| WO | WO-2008/150840 | 12/2008 |
| WO | WO 2009/126112 A1 | 10/2009 |
| WO | WO-2010/099289 A1 | 9/2010 |
| WO | WO-2012/078636 | 6/2012 |
| WO | WO-2012/100221 | 7/2012 |
| WO | WO-2012/100225 A1 | 7/2012 |
| WO | WO-2012/106677 A2 | 8/2012 |
| WO | WO-2013/110668 A1 | 8/2013 |
| WO | WO-2014/143891 A1 | 9/2014 |

OTHER PUBLICATIONS

Adelson, E. et al., Pyramid Methods in Image Processing. RCA Engineer. 1984; 29(6):33-41.

Agurto et al., Detection and phenotyping of retinal disease using AM-FM processing for feature extraction. Signals, Systems and Computers, 2008 42nd Asilomar Conference on. IEEE, 2008.

Agurto et al., Multiscale AM-FM Methods for Diabetic Retinopathy Lesion Detection. Feb. 2010, Medical Imaging, IEEE Trans. 29(2):502-12.

Barriga et al., Automatic system for diabetic retinopathy screening based on AM-FM, partial least squares, and support vector machines.

(56) References Cited

OTHER PUBLICATIONS

Apr. 2010, Biomedical Imaging: From Nano to Macro, 2010 IEEE International Symposium. pp. 1349-52.
Barriga et al., Multi-scale AM-FM for lesion phenotyping on age-related macular degeneration. Computer-Based Medical Systems, 2009. CBMS 2009. 22nd IEEE International Symposium on. IEEE, 2009.
Boroujeni et al., Coronary Artery Center-line Extraction Using Second Order Local Features. Comput Math Methods Med. 2012 (20 pages).
Can, A. et al., A Feature-based Robust, Hierarchical, Algorithm for Registering Pairs of Images of the Curved Human Retina. IEEE Trans on Pattern analysis and Machine Intelligence. 2002; 24:347-64.
Can, A. et al., A Feature-based Technique for Joint, Linear Estimation of High-Order Image-to-Mosaic Transformations: Mosaicing the Curved Human Retina. IEEE Trans on Pattern Analysis and Machine Intelligence. 2002; 24(3):412-9.
Can, A. et al., Rapid Automated Tracing and Feature Extraction from Retinal Fundus Images Using Direct Exploratory Algorithms. IEEE Trans on Information Technology in Biomedicine. 1999; 3:125-38.
Chanwimaluang, T., Hybrid Retinal Image Registration. IEEE Trans on Information Technology in Biomedicine. 2006; 10:129-42.
Choe, T. et al., Optimal Global Mosaic Generation from Retinal Images. Int Conf on Pattern Recognition. 2006; 3:681-4.
Chrástek et al., Automated Calculation of Retinal Arteriovenous Ratio for Detection and Monitoring of Cerebrovascular Disease Based on Assessment of Morphological Changes of Retinal Vascular System. MVA 2002 Proc IAPR Workshop Machine Vision App. 2002; pp. 240-243.
Chrástek et al., Automated Segmentation of the Optic Nerve Head for Diagnosis of Glaucoma. Med Image Anal. 2005; pp. 297-314.
Deng, K. et al., Retinal Fundus Image Registration via Vascular Structure Graph Matching. Int J Biomed Imag. 2010. (19 pages).
Eye Conditions Encyclopedia, "Optic Nerve Imaging"; EyeMDLink. com; Dec. 3, 2005; pp. 1-2.
Frangi et al., Multiscale Vessel Enhancement Filtering. Medical Image Computing and Computer- Assisted Intervention—MICCAI'98 Lecture Notes in Computer Sci. 1998; 1496:130-7.
Ginneken et al., IOP Image Processing Project Proposal: Computer-aided Diagnosis for Diabetic Retinopathy Detection in Fundus Images. Apr. 5, 2002; pp. 1-23.
Goatman, K., Automated Detection of Microaneurysms. Abstracts Reports. Biomed Phys Bioeng, University of Aberdeen. Retrieved from: <www.biomed.abdn.ac.uk/Abstracts/A07890/>. Jul. 10, 1997 (8 pages).
Ter Haar Romeny, B.M., Front-End Vision and Multi-Scale Image Analysis. Springer: 2003, pp. xiii-xviii.
Hackel, R. and Saine, P., Creating Retinal Fundus Maps. J Ophthalmic Photography. 2005; 27(1):10-8.
Huang et al., Development and Comparison of Automated Classifiers for Glaucoma Diagnosis Using Stratus Optical Coherence Tomography. Invest Ophthalmol Visual Sci. 2005; 46(11):4121-9.
Hyvärinen, A. and Oja, E., Independent Component Analysis: Algorithms and Applications. Neural Netw. 2000; 13(4-5):411.30.
Johnson et al., Structure and Function Evaluation (Safe): II. Comparison of Optic Disk and Visual Field Characteristics. Am J Ophthalmol. 2003; 135(2):148-54.
Klein, B.E. et al., Cardiovascular Disease, Mortality, and Retinal Microvascular Characteristics in Type 1 Diabetes. Arch Intern Med. 2004; 164(17):1917-24.
Kondermann et al., Blood Vessel Classification into Arteries and Veins in Retinal Images. Proc SPIE. 2007; 6512:651247-1 to 651247-9.
Lee et al., Retinal atlas statistics from color fundus images. Med Imaging: Image Processing. 2010 (10 pages).
Light Shaping Diffusers Including a Rear Projection System. Physical Optics Corp. 2003. Reprinted from the Aug. 1996 issue of Photonics Spectra © Laurin Publishing Co., Inc. [Retrieved on Apr. 15, 2010]. Retrieved from the Internet: <URL: http://www.poc.com/isd/default.asp?page=applications&sub=dst> p. 1. paragraph 7 (3 pages).
Lliev et al., Morphometric Assessment of Normal, Suspect and Glaucomatous Optic Discs with Stratus OCT and HRT II. Eye. 2005; pp. 1-12.
Maintz, J. and Viergever, M., A Survey of Medical Image Registration. Medical Image Analysis. 1998; 2(1):1-36.
Martus et al., Multivariate Approach for Quantification of Morphologic and Functional Damage in Glaucoma. Invest Ophthalmol Visual Sci. 41(5):1099-110.
Muramatsu et al., Automated selection of major arteries and veins for measurement of arteriolar-to-venular diameter ratio on retinal fundus images. Comp Med Imaging Graphics. 2011; 35(6):472-80.
Niemeijer, M. et al., Automatic determination of the artery-vein ratio in retinal images. Proc SPIE—The Int Soc Optic Eng. 2010; 7624: 762401-1 to 762401-10.
Quellec et al., Optimal Filter Framework for Automated, Instantaneous Detection of Lesions in Retinal Images. Oct. 21, 2010, Medical Imaging, IEEE Transactions on, 30(2): 523-33.
Quellec et al., Optimal wavelet transform for the detection of microaneurysms in retina photographs. IEEE Trans Med Imaging 27.9. 2008; 1230-41.
Ritter, N. et al., Registration of Stereo and Temporal Images of the Retina. IEEE Trans on Medical Imaging. 1999; 18:404-18.
"Segmentation"; Image Processing Fundamentals—Segmentation; Website: www.ph.tn.tudelft.nl/Courses/FIP/frames/fip-Segmenta. html; pp. 1-9.
Sharrett, A.R. et al., Retinal Arteriolar Diameters and Elevated Blood Pressure. Am J Epidemiol. 1999; 150(3):263-70.
Staal, J. et al., Ridge-based Vessel Segmentation in Color Images of the Retina. IEEE Trans on Medical Imaging. 2004; 23(4):501-9.
Swindale et al., Automated Analysis of Normal and Glaucomatous Optic Nerve Head Topography Images. Invest Ophthalmol Visual Sci. 2000; 41(7):1730-42.
Szymczak et al., Coronary Vessel Trees from 3D Imagery: a Topographical Approach. Med Image Anal. 2006; 10(4):548-59.
Toderici, G. et al., Evaluation of Variability and Significance of Fundus Camera Lens Distortion. Proc 26th Annual Int Conf of the IEEE Eng in Med and Bo Soc. pp. 1-5 (San Francisco, CA; Sep. 2004).
Tuytelaars et al., Matching widely separated views based on affine invariant regions. Int J Comp Vision 59.1. 2004; pp. 61-85.
Vincent, L., Morphological Grayscale Reconstruction in Image Analysis: Applications and Efficient Algorithms. IEEE Trans on Image Processing. 1993; 2:176-201.
Weng, J. et al., Camera Calibration with Distortion Models and Accuracy Evaluation. IEEE Trans on Pattern Analysis and Machine Intelligence. 1992; 14(10):965-80.
Wong et al., Computer-Assisted Measurement of Retinal Vessel Diameters in the Beaver Dam Eye Study Methodology: Correlation Between Eyes and Effect of Refractive Errors. Ophthalmology. 2004; 111(6):1183-90.
Xu, J. and Chutatape, O., Comparative Study of Two Calibration Methods on Fundus Camera. Proc 26th Annual Int Conf of the IEEE Eng in Med and Bio Soc. pp. 576-579 (Cancun, Mexico; 2003).
Yale Medicine Winter/Spring 1998, Imaging the Eye. Medicine's New Eyes. pp. 1-3.
Zomet, A., Seamless Image Stitching by Minimizing False Edges. IEEE Trans on Image Processing. 2006; 15:969-77.
International Search Report and Written Opinion issued on Jan. 3, 2008 by the International Searching Authority for Patent Application No. PCT/US2006/012191, which was filed on Mar. 31, 2006 and published as WO 2006/105473 on Oct. 5, 2006 (Inventor—Abramoff et al.; Applicant—University of Iowa Research Foundation et al.) (7 pages).
International Preliminary Report on Patentability issued on Mar. 10, 2009 by the International Searching Authority for Patent Application No. PCT/US2006/012191, which was filed on Mar. 31, 2006 and published as WO 2006/105473 on Oct. 5, 2006 (Inventor—Abramoff et al.; Applicant—University of Iowa Research Foundation et al.) (6 pages).

(56) References Cited

OTHER PUBLICATIONS

International Search Report and Written Opinion mailed on Sep. 17, 2008 by the International Searching Authority for Patent Application No. PCT/US2007/065862, which was filed on Apr. 3, 2007 and published as WO 2007/118079 on Oct. 18, 2007 (Inventor—Abramoff et al.; University of Iowa Research Foundation et al.) (4 pages).
International Preliminary Report on Patentability issued on Nov. 4, 2008 by the International Searching Authority for Patent Application No. PCT/US2007/065862, which was filed on Apr. 3, 2007 and published as WO 2007/118079 on Oct. 18, 2007 (Inventor—Abramoff et al.; University of Iowa Research Foundation et al.) (4 pages).
International Search Report and Written Opinion mailed on Oct. 15, 2008 by the International Searching Authority for Patent Application No. PCT/US2008/065043, which was filed on May 29, 2008 and published as WO 2008/150840 on Dec. 11, 2008 (Inventor—Abramoff et al.; Applicant—University of Iowa Research Foundation) (6 pages).
International Preliminary Report on Patentability issued Dec. 1, 2009 by the International Searching Authority for Patent Application No. PCT/US2008/065043, which was filed on May 29, 2008 and published as WO 2008/150840 on Dec. 11, 2008 (Inventor—Inventor—Abramoff et al.; Applicant—University of Iowa Research Foundation) (5 pages).
International Search Report and Written Opinion mailed on May 3, 2010 by the International Searching Authority for Patent Application No. PCT/US2010/025369, which was filed on Feb. 25, 2010 and published as WO 2010/099289 on Sep. 2, 2010 (Inventor—Abramoff et al.; Applicant—University of Iowa Research foundation) (9 pages).
International Preliminary Report on Patentability issued on Aug. 30, 2011 by the International Searching Authority for Patent Application No. PCT/US2010/025369, which was filed on Feb. 25, 2010 and published as WO 2010/099289 on Sep. 2, 2010 (Inventor—Abramoff et al.; Applicant—University of Iowa Research foundation) (8 pages).
International Search Report and Written Opinion was mailed on Apr. 3, 2012 by the International Searching Authority for Application No. PCT/US2011/63537, which was filed on Dec. 6, 2011 and published as WO 2012/078636 on Jun. 14, 2012 (Inventor—Abramoff et al.; Applicant—University of Iowa Research Foundation) (11 Pages).
International Preliminary Report on Patentability was mailed on Jun. 12, 2013 by the International Searching Authority for Application No. PCT/US2011/63537, which was filed on Dec. 6, 2011 and published as WO 2012/078636 on Jun. 14, 2012 (Inventor—Abramoff et al.; Applicant—University of Iowa Research Foundation) (10 Pages).
Preliminary Amendment was mailed on Jun. 7, 2013 to the U.S. Patent and Trademark Office for U.S. Appl. No. 13/992,552, filed Jul. 25, 2013 and published as US 2013/0301889 on Nov. 4, 2013 (Inventor—Abramoff et al.; Applicant—University of Iowa Research Foundation) (8 Pages).
Non Final Rejection was issued on May 11, 2015 by the U.S. Patent and Trademark Office for U.S. Appl. No. 13/992,552, filed Jul. 25, 2013 and published as US 2013/0301889 on Nov. 4, 2013 (Applicant—University of Iowa Research Foundation; Inventor—Abramoff et al.) (31 Pages).
Response to Non Final Rejection was mailed on Oct. 12, 2015 to the U.S. Patent and Trademark Office for U.S. Appl. No. 13/992,552, filed Jul. 25, 2013 and published as US 2013/0301889 on Nov. 4, 2013 (Applicant—University of Iowa Research Foundation; Inventor—Abramoff, et al.) (12 Pages).
Final Rejection was issued on Nov. 13, 2015 by the U.S. Patent and Trademark Office for U.S. Appl. No. 13/992,552, filed Jul. 25, 2013 and published as US 2013/0301889 on Nov. 4, 2013 (Applicant—University of Iowa Research Foundation; Inventor—Abramoff et al.) (32 Pages).

Non Final Rejection was issued on Jul. 11, 2016 by the U.S. Patent and Trademark Office for U.S. Appl. No. 13/992,552, filed Jul. 25, 2013 and published as US 2013/0301889 on Nov. 4, 2013 (Applicant—University of Iowa Research Foundation; Inventor—Abramoff et al.) (37 Pages).
Final Rejection was issued on Mar. 28, 2017 by the U.S. Patent and Trademark Office for U.S. Appl. No. 13/992,552, filed Jul. 25, 2013 and published as US 2015/0379708 on Dec. 31, 2015 (Inventor—Abramoff et al.; Applicant—University of Iowa Research Foundation) (39 pages).
Non-Final Office Action issued on Dec. 11, 2017 by the U.S. Patent and Trademark Office for U.S. Appl. No. 13/992,552, filed Jul. 25, 2013 and published as US 2015/0379708 on Dec. 31, 2015 (Inventor—Abramoff et al.; Applicant—University of Iowa Research Foundation) (33 pages).
Notice of Allowance issued on Jul. 11, 2018 by the U.S. Patent and Trademark Office for U.S. Appl. No. 13/992,552, filed Jul. 25, 2013 and published as US 2015/0379708 on Dec. 31, 2015 (Inventor—Abramoff et al.; Applicant—University of Iowa Research Foundation) (8 pages).
International Search Report and Written Opinion mailed on May 8, 2012 by the International Searching Authority for Patent Application No. PCT/US2012/022115, which was filed on Jan. 20, 2012 and published as WO 2012/100225 on Jul. 26, 2012 (Inventor—Abramoff et al.; Applicant—University of Iowa Research Foundation) (6 pages).
International Preliminary Report on Patentability issued on Jul. 23, 2013 by the International Searching Authority for Patent Application No. PCT/US2012/022115, which was filed on Jan. 20, 2012 and published as WO 2012/100225 on Jul. 26, 2012 (Inventor—Abramoff et al.; Applicant—University of Iowa Research Foundation) (5 pages).
European Search Report issued on Mar. 16, 2016 by the European Patent Office for Application No. 12736290.3, which was filed on Jan. 20, 2011, and published as 2665406, on Nov. 27, 2013 (Inventor—Abramoff et al.; Applicant—University of Iowa Research Foundation) (11 Pages).
International Search Report and Written Opinion mailed on May 25, 2012 by the International Searching Authority for Application No. PCT/US2012/022111, which was filed on Jan. 20, 2012 and published as WO 2012/100221 on Jul. 26, 2012 (Inventor—Abramoff et al.; Applicant—University of Iowa Research Foundation) (7 Pages).
International Preliminary Report on Patentability was mailed on Jul. 23, 2013 by the International Searching Authority for Application No. PCT/US2012/022111, which was filed on Jan. 20, 2012 and published as WO 2012/100221 on Jul. 26, 2012 (Inventor—Abramoff et al.; Applicant—University of Iowa Research Foundation) (6 Pages).
Preliminary Amendment was mailed on Jun. 19, 2012 to the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (3 Pages).
Non Final Rejection was issued on Sep. 19, 2013 by the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (16 Pages).
Response to Non Final Rejection was mailed on Dec. 19, 2013 to the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff f et al.) (10 Pages).
Final Rejection was issued on Mar. 11, 2014 by the U.S. Patent and Trademark Office for U.S. Appl. No. 13/355,386, filed Jan. 20, 2012 and published as US 2012/0236259 on Sep. 20, 2012(Applicant—University of Iowa Research Foundation; Inventor—Abramoff et al.) (17 Pages).
Non Final Rejection was issued on Feb. 6, 2015 by the U.S. Patent and Trademark Office for U.S. Appl. No. 13/355,386, filed Jan. 20,

(56) References Cited

OTHER PUBLICATIONS

/2012 and published as US 2012/0236259 on Sep. 20, 2012 (Applicant—University of Iowa Research Foundation; Inventor—Abramoff et al.) (13 Pages).
Response to Non Final Rejection was mailed on May 6, 2015 to the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (11 Pages).
Final Rejection issued on Jun. 23, 2015 by the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (17 Pages).
Response to Final Rejection mailed on Aug. 24, 2015 to the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (11 Pages).
Non Final Rejection issued on Mar. 30, 2016 by the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (12 Pages).
Response to Non Final Rejection mailed on Sep. 30, 2016 to the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff f et al.) (9 Pages).
Final Rejection issued on Nov. 9, 2016 by the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (14 Pages).
Notice of Allowance issued on Nov. 8, 2017 by the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.)(8 Pages).
Issue Notification issued on Mar. 7, 2018 by the U.S. Patent and Trademark Office for U.S. Appl. No. 13/355,386, filed Jan. 20, 2012 and published as US 2012/0236259 on Sep. 20, 2012 (Applicant—University of Iowa Research Foundation; Inventor—Abramoff et al.) (1 Page).
International Search Report and Written Opinion mailed on Sep. 4, 2014 by the International Searching Authority for Application No. PCT/US2014/014298, which was filed on Jan. 31, 2014 and published as WO/2014/158345 on Oct. 2, 2014 (Applicant—University of Iowa Research Foundation) (7 Pages).
International Preliminary Report on Patentability mailed on Aug. 4, 2015 by the International Searching Authority for Application No. PCT/US2014/014298, which was filed on Jan. 31, 2014 and published as WO/2014/158345 on Oct. 2, 2014 (Inventor—Abramoff et al.; Applicant—University of Iowa Research Foundation) (6 Pages).
Preliminary Amendment mailed on Jul. 30, 2015 to the U.S. Patent and Trademark Office for U.S. Appl. No. 14/764,926, filed Jul. 30, 2015 and published as US 2015/0379708 on Dec. 31, 2015 (Applicant—University of Iowa Research Foundation; Inventor—Abramoff et al.) (4 Pages).
Non Final Rejection issued on Jan. 27, 2017 by the U.S. Patent and Trademark Office for U.S. Appl. No. 14/764,926, filed Jul. 30, 2015 and published as US 2015/0379708 on Dec. 31, 2015 (Applicant—University of Iowa Research Foundation; Inventor—Abramoff et al.) (9 Pages).
International Search Report and Written Opinion mailed on Aug. 15, 2014 by the International Searching Authority for Application No. PCT/US2014/28055, which was filed on Mar. 14, 2014 and published as WO 2014/143891 on Sep. 18, 2014 (Inventor—Abramoff et al.; Applicant—University of Iowa Research Foundation) (6 Pages).
International Preliminary Report on Patentability was mailed on Sep. 15, 2015 by the International Searching Authority for Application No. PCT/US2014/28055, which was filed on Mar. 14, 2014 and published as WO 2014/143891 on Sep. 18, 2014 (Inventor—Abramoff et al.; Applicant—University of Iowa Research Foundation) (5 Pages).
Non Final Rejection was issued on Nov. 4, 2016 by the U.S. Patent and Trademark Office for U.S. Appl. No. 14/774,801, filed Sep. 11, 2015 and published as US 2016/0035088 on Feb. 4, 2016 (Applicant—University of Iowa Research Foundation; Inventor—Abramoff et al.) (6 Pages).
Preliminary Amendment was mailed on Sep. 11, 2015 to the U.S. Patent and Trademark Office for U.S. Appl. No. 14/774,801, filed Sep. 11, 2015 and published as US 2016/0035088 on Feb. 4, 2016 (Applicant—University of Iowa Research Foundation; Inventor—Abramoff et al.) (4 Pages).
Final Office Action issued on May 12, 2017 by the U.S. Patent and Trademark Office for U.S. Appl. No. 14/774,801, filed Sep. 21, 2015 and published as US 2016/0035088 on Feb. 4, 2016 (Applicant—University of Iowa Research Foundation; Inventor—Abramoff et al.) (7 Pages).
Non-Final Office Action issued on Nov. 17, 2017 by the U.S. Patent and Trademark Office for U.S. Appl. No. 14/774,801, filed Sep. 21, 2015 and published as US 2016/0035088 on Feb. 4, 2016 (Applicant—University of Iowa Research Foundation; Inventor—Abramoff et al.) (8 Pages).
Final Office Action issued on Jul. 23, 2018 by the U.S. Patent and Trademark Office for U.S. Appl. No. 14/774,801, filed Sep. 21, 2015 and published as US 2016/0035088 on Feb. 4, 2016 (Applicant—University of Iowa Research Foundation; Inventor—Abramoff et al.) (8 Pages).
International Search Report and Written Opinion was mailed on Aug. 5, 2015 by the International Searching Authority for Application No. PCT/US2015/022021, which was filed on Mar. 23, 2015 and published as WO 2015/143435 on Sep. 24, 2015 (Inventor—Abramoff et al.; Applicant—University of Iowa Research Foundation) (9 Pages).
International Preliminary Report on Patentability was mailed on Sep. 21, 2016 by the International Searching Authority for Application No. PCT/US2015/022021, which was filed on Mar. 23, 2015 and published as WO 2015/143435 on Sep. 24, 2015 (Inventor—Abramoff et al.; Applicant—University of Iowa Research Foundation) (6 Pages).
Non Final Rejection issued on Dec. 22, 2017 by the U.S. Patent and Trademark Office for U.S. Appl. No. 15/128,035, filed Sep. 21, 2016 and published as US 2017/0098311 on Apr. 6, 2017 (Inventor—Abramoff et al.; Applicant—University of Iowa Research Foundation et al.) (16 pages).
Niemeijer, Meindert, et al. "Automatic Classification of Retinal Vessels into Arteries and Veins." Medical Imaging 2009: Computer-Aided Diagnosis, vol. 7260, Feb. 17, 2009, pp. 72601F-1-72601F-8., doi:10.1117/12.813826 (Year: 2009).
Larry D Hubbard, et al., Methods for evaluation of retinal microvascular abnormalities associated with hypertension/sclerosis in the atherosclerosis risk in communities study; Ophthalmology; vol. 106, Issue 12,1999, pp. 2269-2280 (Year: 1999).
Knudtson MD, Lee KE, Hubbard LD, Wong TY, Klein R, Klein BE. Revised formulas for summarizing retinal vessel diameters. Curr Eye Res. Sep. 2003;27(3):143-9. doi: 10.1076/ceyr.27.3.143.16049 (Year: 2003).
Leung, Harry & Wang, Jie & Rochtchina, Elena & Tan, Ava & Wong, T-Y & Klein, Ronald & Hubbard, Larry & Mitchell, Paul. (2003). Relationships between Age, Blood Pressure, and Retinal Vessel Diameters in an Older Population. Investigative ophthalmology & visual science. 44. 2900-4.10.1167/iovs.02-1114 (Year: 2003).
Gardner et al. "Automatic detection of diabetic retinopathy using an artificial neural network: a screening tool." British journal of Ophthalmology 80.11 (1996): 940-944. (Year: 1996).
Dupas et al. "Evaluation of automated fundus photograph analysis algorithms for detecting microaneurysms, hemorrhages and exudates, and of a computer-assisted diagnostic system for grading diabetic retinopathy." Diabetes & metabolism 36.3 (Mar. 2010 ): 213-220. (Year: 2010).

(56) References Cited

OTHER PUBLICATIONS

Calvo, David, et al. "Automatic Detection and Characterisation of Retinal Vessel Tree Bifurcations and Crossovers in Eye Fundus Images." Computer Methods and Programs in Biomedicine, vol. 103, No. 1, 2011 (online: Jul. 19, 2010), pp. 28-38., https://doi.org/10.1016/j.cmpb.2010.06.002 (Year: 2010).

Calvo, D., et al.(2009). Characterisation of Feature Points in Eye Fundus Images. In: Bayro-Corrochano, E., Eklundh, JO. (eds) Progress in Pattern Recognition, Image Analysis, Computer Vision, and Applications. CIARP 2009. Lecture Notes in Computer Science, vol. 5856. Springer, Berlin, Heidelberg. (Year: 2009).

S. G. Vazquez, B. et al., "On the Automatic Computation of the Arterio-Venous Ratio in Retinal Images: Using Minimal Paths for the ArteryNein Classification," 2010 International Conference on Digital Image Computing: Techniques and Applications, 2010, pp. 599-604 (Year: 2010).

C. Nieuwenhuis and M. Yan, "Knowledge based image enhancement using neural networks," 18th International Conference on Pattern Recognition (ICPR) , pp. 814-817, 2006 (Year: 2006).

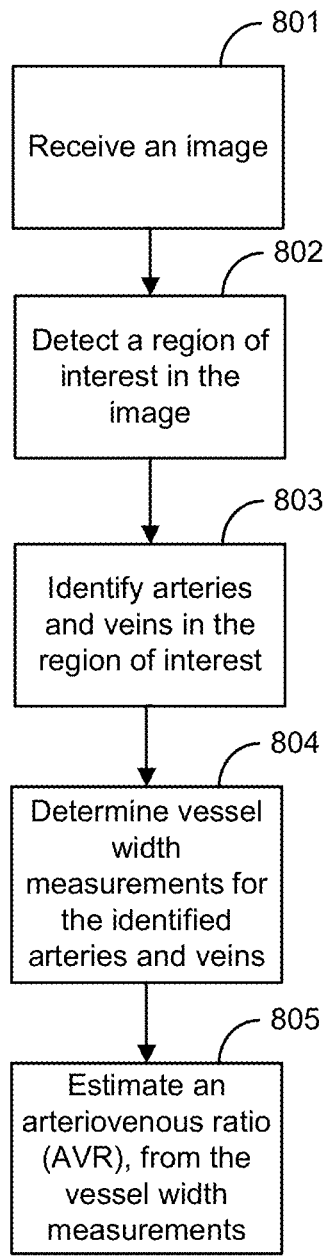

AUTOMATED DETERMINATION OF ARTERIOVENOUS RATIO IN IMAGES OF BLOOD VESSELS

CROSS REFERENCE TO RELATED PATENT APPLICATION

This application is a continuation of U.S. Non-Provisional application Ser. No. 15/936,162, filed on Mar. 26, 2018, which is a continuation of U.S. Non-Provisional application Ser. No. 13/355,386, filed on Jan. 20, 2012, and issued as U.S. Pat. No. 9,924,867 on Mar. 27, 2018, which claims priority to U.S. Provisional Application No. 61/434,551, filed on Jan. 20, 2011, each of which are incorporated by reference in their entireties herein.

GOVERNMENT LICENSE RIGHTS

This invention was made with government support under EY017066 awarded by the National Institutes of Health. The government has certain rights in the invention.

SUMMARY

The methods and systems provided can automatically determine an Arteriolar-to-Venular diameter Ratio, AVR, in blood vessels, such as retinal blood vessels and other blood vessels in vertebrates. The AVR is an important predictor of increases in the risk for stroke, cerebral atrophy, cognitive decline, and myocardial infarct. It can thus be used to perform risk analysis of (a) cardiovascular events in patients already undergoing fundus imaging for other reasons, such as diabetic retinopathy screening, (b) risk analysis for patients undergoing fundus imaging for specifically that reason, or (c) risk analysis in other situations.

The methods and systems provided can predict cardiovascular events. In different embodiments, the methods and systems provided can be applicable in many areas including Medicine, Neurology, Primary Care, Ophthalmology, as well as other applications to determine properties of blood vessels in other parts of the body that are suitable for multi-wavelength imaging, such as the iris, the skin, the eardrum, as well as other organs in albino animals.

Until now, the AVR has always been determined manually from retinal color fundus images, which is a time consuming process requiring an expert. Though clinicians look at the retina, they can only perform gross estimates for substantially abnormal a/v ratios, and are incapable of determining numeric ratios.

A decreased ratio of the width of retinal arteries to veins (Arteriolar-to-Venular diameter Ratio, AVR), can be predictive of medical conditions such as cerebral atrophy, stroke and other cardiovascular events. Tortuous and dilated arteries and veins, as well as decreased AVR can also be a marker for Plus disease in retinopathy of prematurity. In an aspect, the methods and systems provided can estimate the AVR in retinal color images by detecting the location of the optic disc, determining an appropriate region of interest (ROI), classifying vessels as arteries or veins, estimating the widths and calculating the AVR. In a further aspect, after vessel segmentation and vessel width determination, the optic disc is located and the system can eliminate all vessels outside the AVR measurement ROI. A skeletonization operation can be applied to the remaining vessels after which vessel crossings and bifurcation points can be removed, leaving a set of vessel segments that are vessel centerline pixels. Features can be extracted from each centerline pixel in order to assign these a soft label indicating the likelihood the pixel is part of a vein. As all centerline pixels in a connected vessel segment should be the same type, the median soft label can be assigned to each centerline pixel in the segment. Artery/vein pairs can be matched using an iterative algorithm, and the widths of the vessels used to calculate the AVR.

The automated method and systems provided for determination of the AVR can have substantial impact on clinical practice, and an improved assessment for patients at risk for cardiovascular and brain disease.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 8 shows an exemplary flowchart illustrating steps of a method;

DETAILED DESCRIPTION

Figure 1:
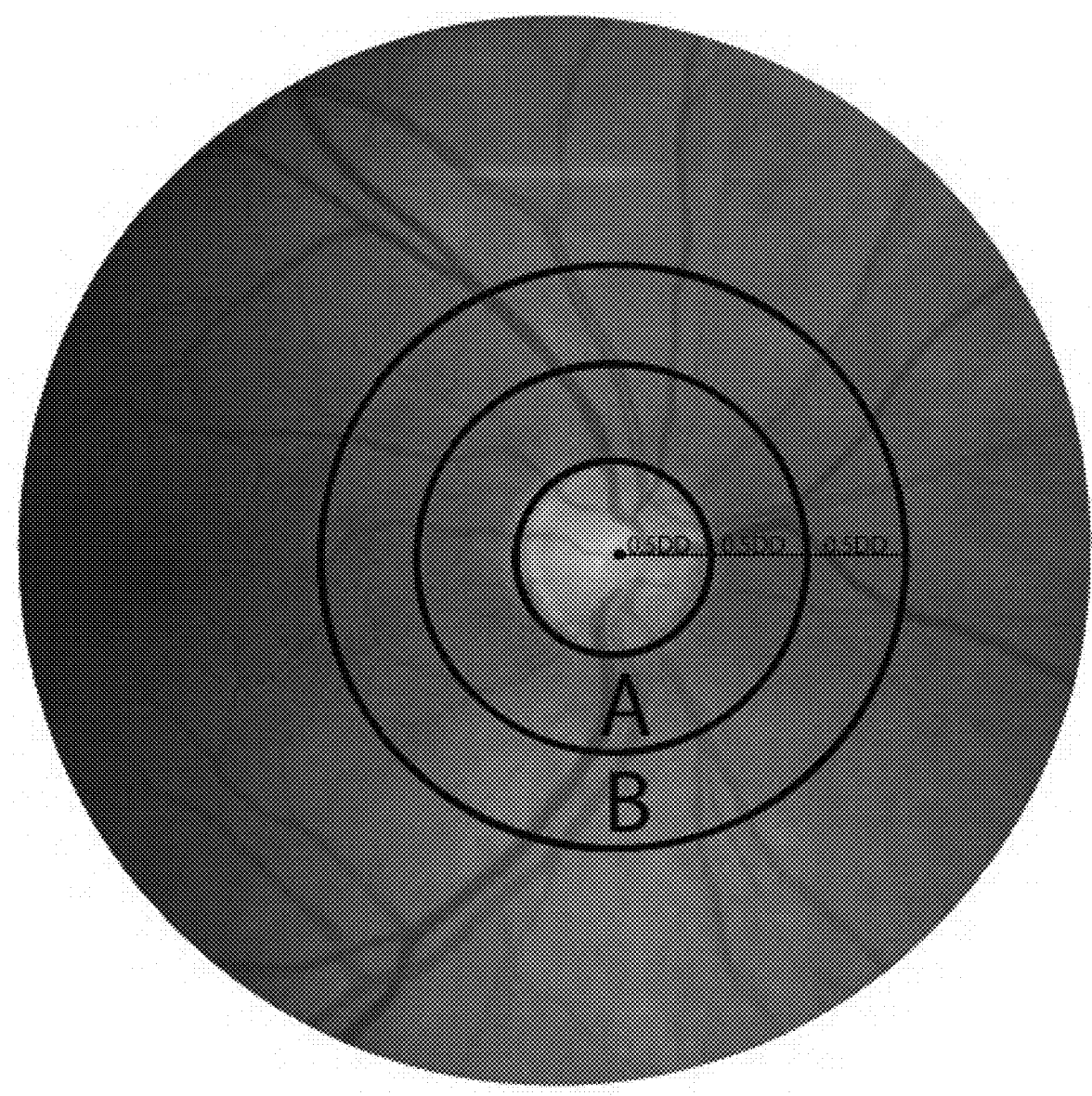
FIG. 1 shows an image overlaid with an automatically determined ROI region.
Figure 2A:
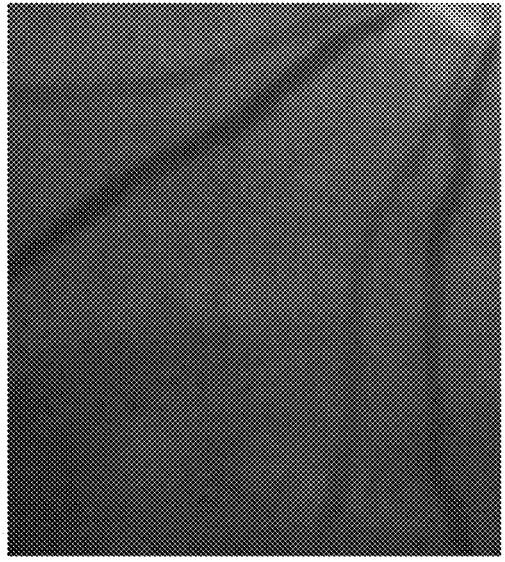
FIG. 2A shows a color fundus image.
Figure 2B:
FIG. 2B shows a vessel likelihood map.
Figure 2C:
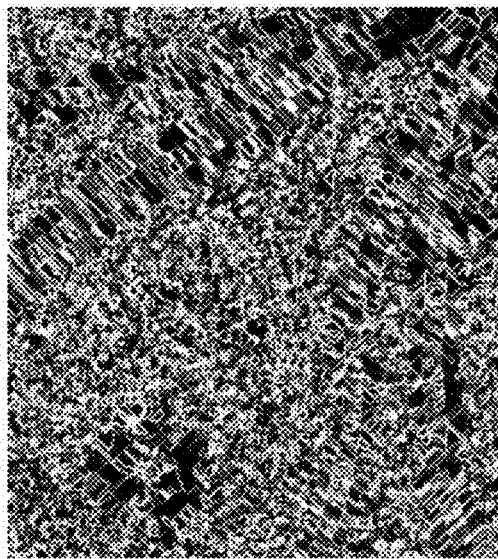
FIG. 2C shows a splat map, the borders of the individual splats are shown.
Figure 2D:
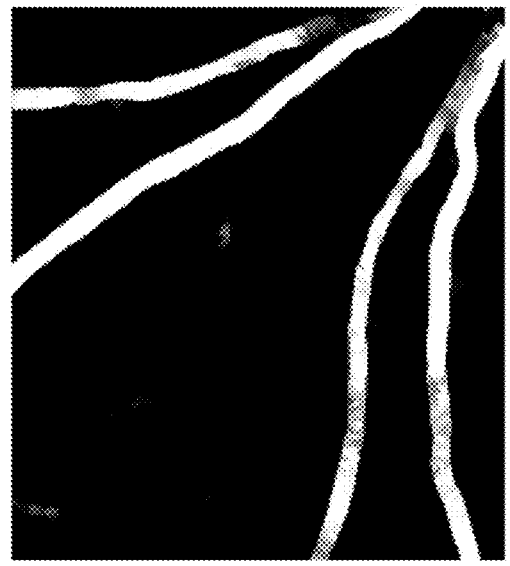
FIG. 2D shows a processed vessel likelihood map.
Figure 2E:
FIG. 2E shows vessel centerlines where each centerline pixel has been assigned the likelihood it is inside a vein (dilated for display)
Figure 2F:
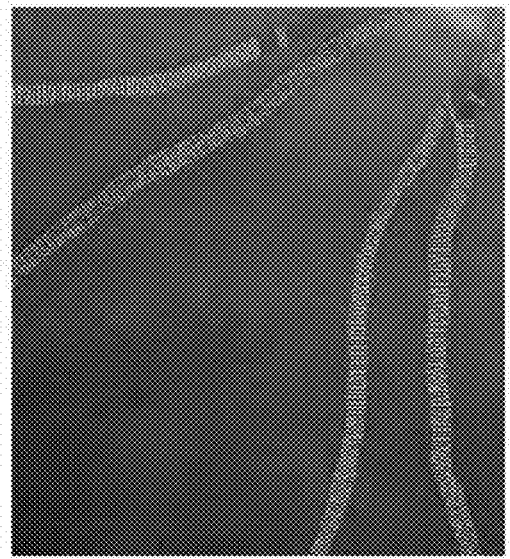
FIG. 2F shows final width measures overlaid on the original image shown in FIG. 2A.

Before the present methods and systems are disclosed and described, it is to be understood that the methods and systems are not limited to specific methods, specific components, or to particular configurations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

In certain aspects, the accurate estimation of AVR can comprise one or more of the following, optic disc detection, vessel segmentation, vessel width measurement, vessel network analysis, and artery/vein classification. Optic disc detection can determine the location of the Region of Interest (ROI) where the measurements are obtained. Vessel segmentation can be used to find the vessels themselves and, depending on the method that is used, the width of the vessels. The methods and systems can then identify which vessels are arteries and which are veins with high accuracy. Small classification errors can have a large influence on the final AVR.

A protocol has been established for the measurement of the AVR. The protocol defines where and how measurements should be obtained. The automated methods and systems described herein follow this protocol whenever possible. In an aspect, the methods and systems can by pre-process an image to remove the gradient around the border of the field of view (FOV) as well as to remove slow intensity variations in the image. Further pre-processing can be focused on the detection of anatomical landmarks. These can comprise the optic disc, the landmark on the retina around which the measurements are obtained and the vasculature, the structure that is actually being measured. Vessel width measurements can be obtained and the vessels within the measurement area can be classified into arteries and veins. Finally, the artery vein ratio can be determined.

A. Preprocessing

The methods and systems can implement one or more preprocessing techniques. For example, Field of View mirroring and background removal. Digital color fundus photographs have a black border around the FOV. The large gradient can disturb feature measurements near the FOV border. It can be removed by applying a mirroring technique. This method mirrors pixel values from within the circular field of view to outside the FOV. This operation can be performed at the original image resolution. Slow background variations can be removed by blurring the image with a Gaussian filter with a large standard deviation and subtracting the blurred image from the original. The value of the standard deviation of the Gaussian filter is not a critical parameter as long as it is large enough to ensure the blurred image contains no visible structures such as vessels. This procedure can be performed on both the Red as well as the Green color planes separately. From here, whenever the Green and Red plane is mentioned, it refers to the pre-processed versions. The Blue color plane is not used.

In an aspect, pixel classification can be used to segment the retinal vasculature. The filter outputs of a Gaussian filter bank can be used as features to train a kNN-classifier to detect the vasculature. This method is not scale independent as the Gaussian filterbank features are extracted at particular scales. Additionally, the images with which the vessel segmentation method can be trained (for example, the DRIVE database as is known to one of skill in the art) have a particular resolution and therefore a particular range of vessel widths (measured in pixels). In a further aspect, images can be downsampled before applying the vessel segmentation, for example with a factor 4.

In an aspect, the vessel segmentation method can assign each pixel in the image a likelihood between 0 and 1 that the pixel is within a vessel. This results in a "vesselness map" that can be thresholded to produce a binary vessel segmentation. In an aspect, prior to thresholding the vesselness map can be up sampled back to the resolution of the original image, for example by using quintic spline interpolation. To analyze the vessel network a skeletonization method can be applied to the thresholded likelihood map, reducing all vessels to a single centerline. In an aspect, the centerline can be one or more pixels wide. After the skeletonization of the segmented vessels, cross-over and bifurcation points can be removed by counting the number of neighbors for all centerline pixels and removing those with more than two neighbors. This operation subdivides the vascular network into a collection of vessel segments that can be individually analyzed.

In an aspect, a supervised position regression method can be used to detect the centerpoint of the optic disc. This method can estimate how far a certain position in the image is from the optic disc center. This estimation can be based on measurements obtained in the image and from the vessel segmentation. The target location can be found by obtaining estimates in many locations in the image, eliminating those locations that are estimated to be far from the optic disc and searching around the locations estimated to be close to the optic disc center. The method can first be trained using a large set of images for which the location of the optic disc is known. As this method does not provide an estimate of the size of the optic disc, a more or less constant size can be assumed. For example, a value of 360 pixels can be used for the diameter of the optic disc (DD). Other diameters can be used and determined by those of skill in the art.

The AVR calculation protocol defines the region of interest (ROI) in which the AVR should be measured. This ROI is centered on the optic disc (see FIG. 1). FIG. 1 shows an image overlaid with the automatically determined ROI region. The region labeled "B" is where AVR measurements are taken. The ROI comprises several circular regions whose size is based on the approximate diameter of the optic disc. Region A is between 0.5 and 1 DD from the optic disc center and region B, where vessel measurements are taken, is between 1DD and 1.5DD from the optic disc center. In an aspect, all analysis and evaluation performed by the methods and systems is within region B, however, it may be advantageous to expand or contract the region within which the methods and systems can operate.

B. Vessel Width Measurement

In an aspect, after preprocessing, the vasculature can be thinned and subdivided into a set of vessel segments. All vessel segments that are not (partly) inside region B (FIG. 1) can be removed as they are not used in the AVR analysis. Even though the vessel segmentation method provided can successfully localize most vessels, i.e. wide and narrow ones, choosing a single threshold to produce a binary segmentation of the vasculature that can be used to determine the local vessel width is difficult. The values in the likelihood map, as produced by the vessel segmentation method, tend to zero as one moves away from the vessel border into the retinal background. This effect is also dependent on the vessel width with narrower vessels having an overall lower likelihood response than wider vessels. Consequently, relatively small variations in the applied threshold result in substantial vessel width differences and thresholds that give visually pleasing results for wider vessels completely miss smaller vessels. This is further complicated by the fact that the vessel detection is performed at a lower resolution resulting in larger errors after upsampling.

In an aspect, a technique referred to as tobogganing can be combined with vessel segmentation. This has the added benefit that vessel width analysis can be performed on the original images in their original resolution. Tobogganing is a segmentation technique that subdivides the image into areas (i.e. "splats") that are homogeneous based on a certain criterion. The technique's results are analogous to the "catchment basins" in watershed segmentation. The multi-scale gradient magnitude image can be used to define homogeneity. To calculate the gradient magnitude, the image can be convolved with a first derivative of Gaussian filter in both the x and y direction after which the magnitude of the gradient is obtained for each pixel. The gradient magnitude at various scales (i.e. various standard deviations $\sigma$) tends to have a maximum at the border of high contrast structures such as the vasculature. A lower scale filter can give more response at the border of small vessels and a higher scale filter can give more response at the border of wider vessels. To obtain the multiscale gradient magnitude image the scale-normalized gradient magnitude can be calculated at scales σ=1, 2, 3, 4, 5, 6 and the maximum value over scale for each of the pixels in the image can be used. After applying the tobogganing method, a splat map (see FIG. 2c) can be obtained. The likelihood map produced by the vessel segmentation algorithm can now be used to determine for each splat the likelihood it is inside a vessel. This can be accomplished by assigning to each splat the median likelihood value of all the pixels that are part of the splat. It can be assumed the splats are either inside or outside the vessel (note that this assumption does not always hold in the case of low contrast, narrow vessels). Given a correct likelihood map, this results in the splats inside the vessel being assigned a higher likelihood than those outside the vessel. In the resulting vessel map, the borders of the vessels are better defined and the widths of the vessels become less dependent on the chosen vessel segmentation threshold. This enhanced vessel map can be used to determine the vessel width. FIG. 2 shows the process in more detail on a small subimage.

FIG. 2 is an image showing various processing steps described herein on a small sub-image. FIG. 2a, the color fundus image. FIG. 2b, the vessel likelihood map. A higher pixel value in this image means a higher vessel likelihood. FIG. 2c, the splat map, the borders of the individual splats are shown. FIG. 2d, the processed vessel likelihood map each splat has been assigned the median vessel likelihood value under the splat. FIG. 2e, the vessel centerlines where each centerline pixel has been assigned the likelihood it is inside a vein (dilated for display). FIG. 2f, the final width measures overlaid on the original image. Only every third measurement was plotted.

Figure 3A:
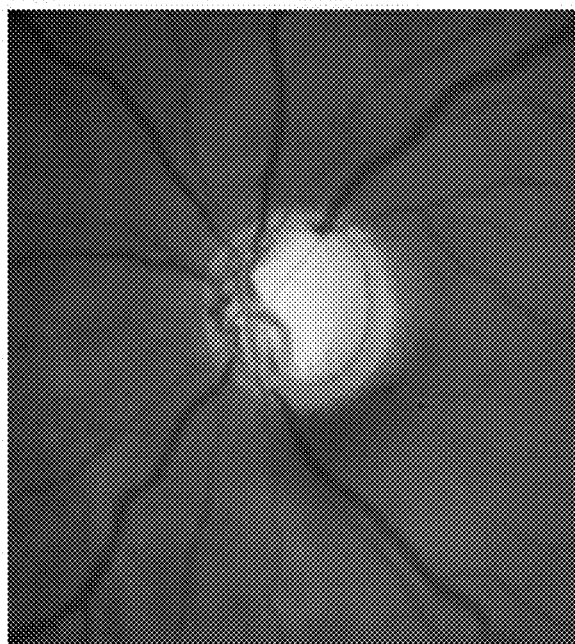
FIG. 3A shows a retinal image.
Figure 3B:
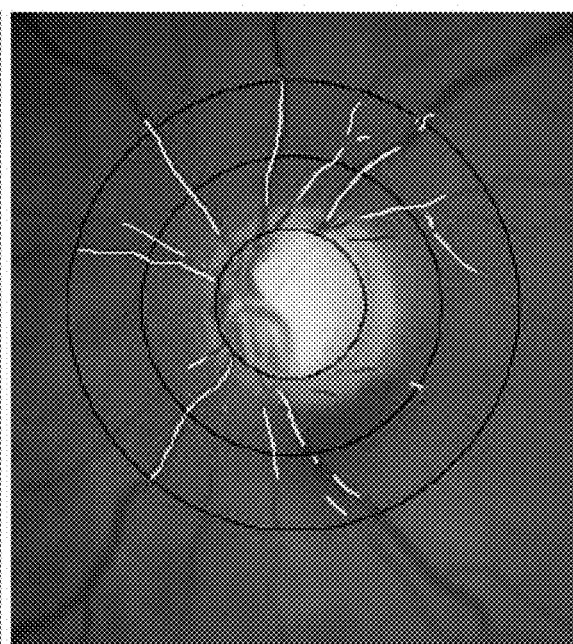
FIG. 3B shows an artery vein centerline classification result overlaid on the retinal image shown in FIG. 3A.

In an aspect, measurement of the local vessel width can be performed perpendicular to the local vessel angle in order to minimize errors during the measurement process. The local vessel angle can be determined for all centerline pixels in every vessel segment. The local vessel angle can be defined as the direction of the largest eigenvector of the covariance matrix of the coordinate of the centerline pixel along with the coordinates of its seven connected neighbors to both sides (i.e. 15 coordinates in total). As it is unknown where the vessel begins or ends, the range of the angles is [0 . . . π]. Near the end of the vessel segment only centerline coordinates inside the vessel are used, 8 for the end pixel. Other values can be determined and used by those of skill in the art. FIG. 3 illustrates an artery vein centerline classification result (FIG. 3b) overlaid on a retinal image (FIG. 3a). A centerline pixel with higher pixel intensity can have a higher likelihood to be a vein.

In an aspect, for each centerline pixel, the local vessel width can be measured by finding the left and right vessel edges in the enhanced vessel map and calculating the distance between them. To determine the locations of the edges of the vessel, the likelihood can be measured along a line through the centerline pixel and perpendicular to the local vessel angle. Starting from the centerline pixel, the vessel border can be found in both left and right direction. The likelihood threshold at which a splat is no longer part of a vessel can be a critical parameter in this algorithm. As the likelihood assigned to vessel splats varies over the image and is dependent on local vessel contrast and vessel width, a local vessel threshold can be determined for every centerline pixel. The vessel likelihood under the centerline pixel can be multiplied with a ratio, for example 0.7, to determine the appropriate value for the vessel threshold.

Figure 4:
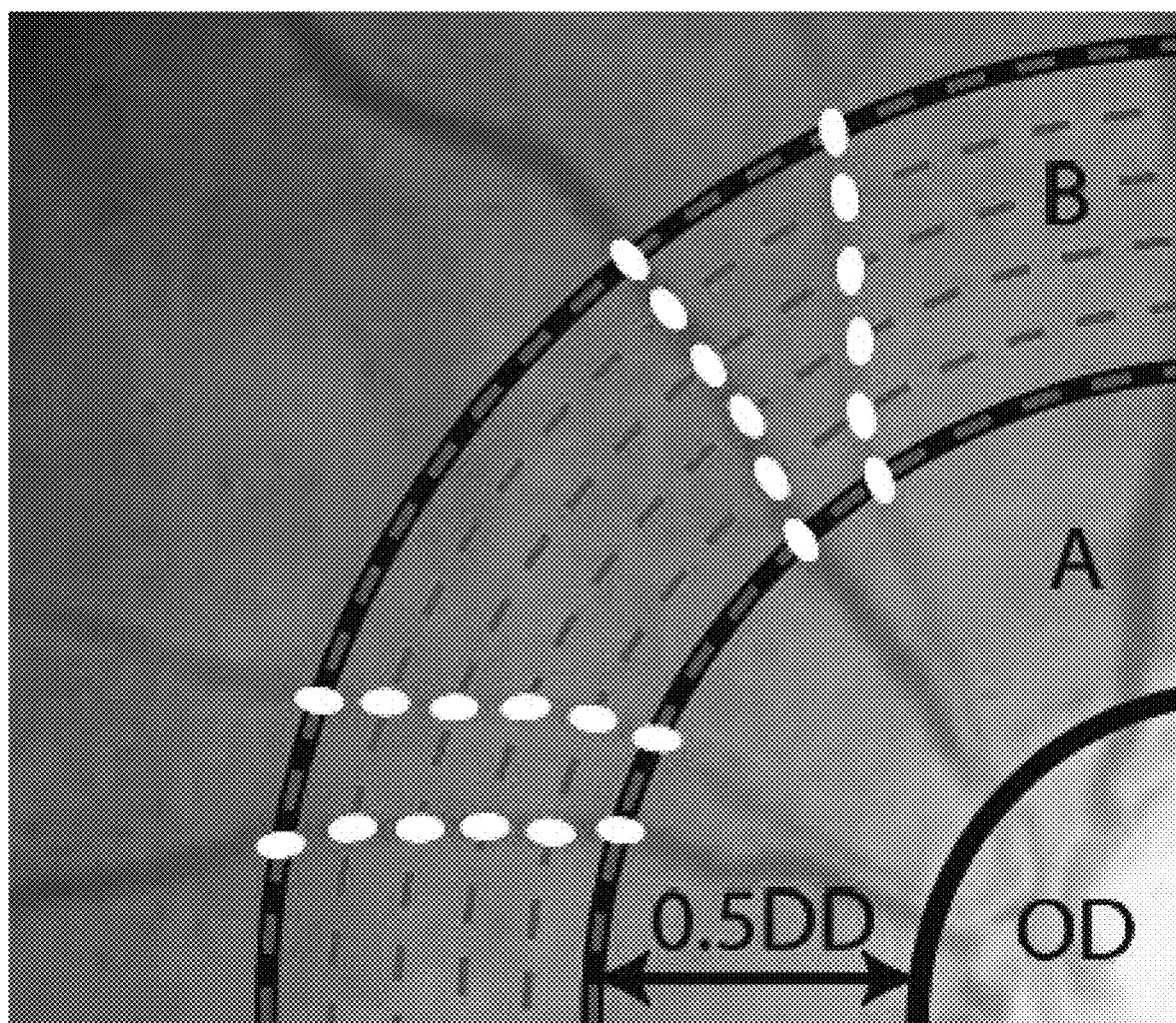
FIG. 4 shows a detail of a fundus photograph showing the measurement diameters and the vessel crossings where width measurements are obtained.

In an aspect, after vessel widths for a vessel segment are determined, error correction can be performed by finding sudden, local changes in the vessel width. A sudden change can be defined as more than a pre-determined number of pixels from one centerline pixel to the other, for example, 3. A sudden change can happen when a vessel splat is not or a background splat is included in the vessel width measurement. The ratio threshold can be varied locally until the width measurement is similar (<3 pixels difference) to the average width at the preceding vessel centerline pixels, for example 8 preceding vessel centerline pixels. If the vessel width can not be adjusted to match the mean width, the originally detected vessel width can be used. FIG. 2 shows width measurement results in a small sub-image. In addition to measuring the vessel width, the location of the left and right vessel boundary for each centerline pixel can be stored. Using these two points, a profile across the vessel can be defined and then used to extract feature data from across the vessel. FIG. 4 is a detail of a fundus photograph showing the measurement diameters and the vessel crossings where width measurements are obtained. The white dots indicate the points on the vessels where measurements are obtained.

In a further aspect, a graph based approach can be used for vessel boundary delineation. A vessel centerline image can be derived from the vesselness map, and the two borders of the vessel can then be segmented simultaneously by transforming the first derivative of the vessel's pixels intensities into a two-slice three-dimension surface segmentation problem. In retinal images, the boundaries of the blood column form a reliable proxy for vessel diameter. While the splat based approach provides reliable results, a graph-based approach to determine the location of the vessel boundary can provide greater speed and accuracy, as graph-based approaches are known to be globally optimal. In addition to AVR analysis, automated determination of vessel width measurement based on segmentation of both vessel boundaries can also allow the geometry of the retinal vessels to be quantified, as the geometry is also affected by cardiovascular disease, diabetes, and retinal disease. Finally, accurate determination of the vessel boundary may allow local pathologic vascular changes such as tortuosity and vessel beading to be measured accurately.

In order to detect both boundaries simultaneously, a two-slice 3-D graph can be built and a smoothness constraint between the two slices can be applied. Thus, a simultaneous two-D boundary segmentation is transformed into a two-slice 3-D surface segmentation problem. This problem is then further converted into the problem of computing a minimum closed set in a node-weighted graph.

Figure 5A:
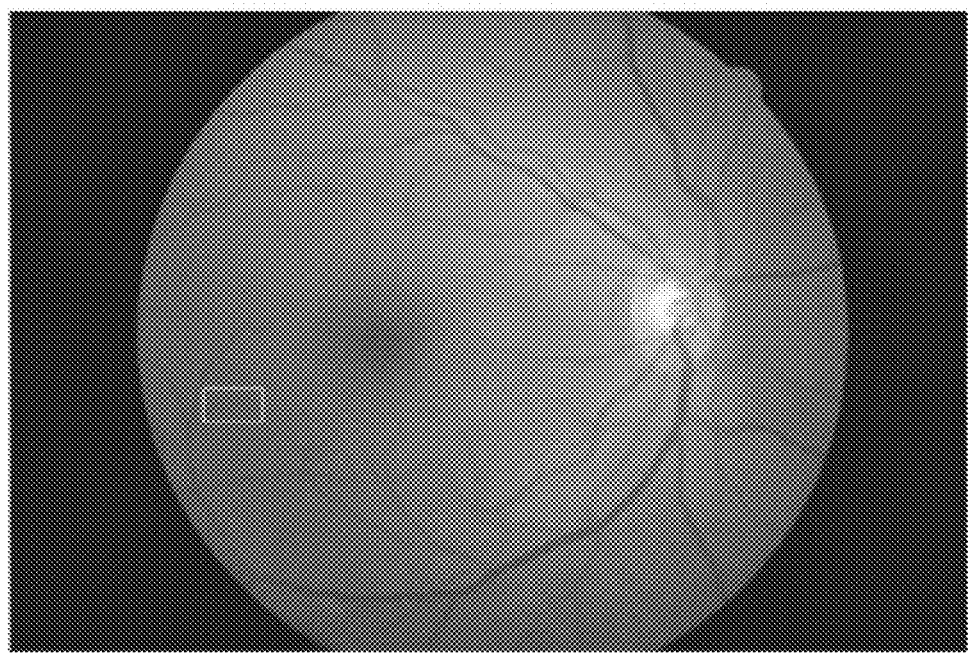
FIG. 5A shows a color fundus image.
Figure 5B:
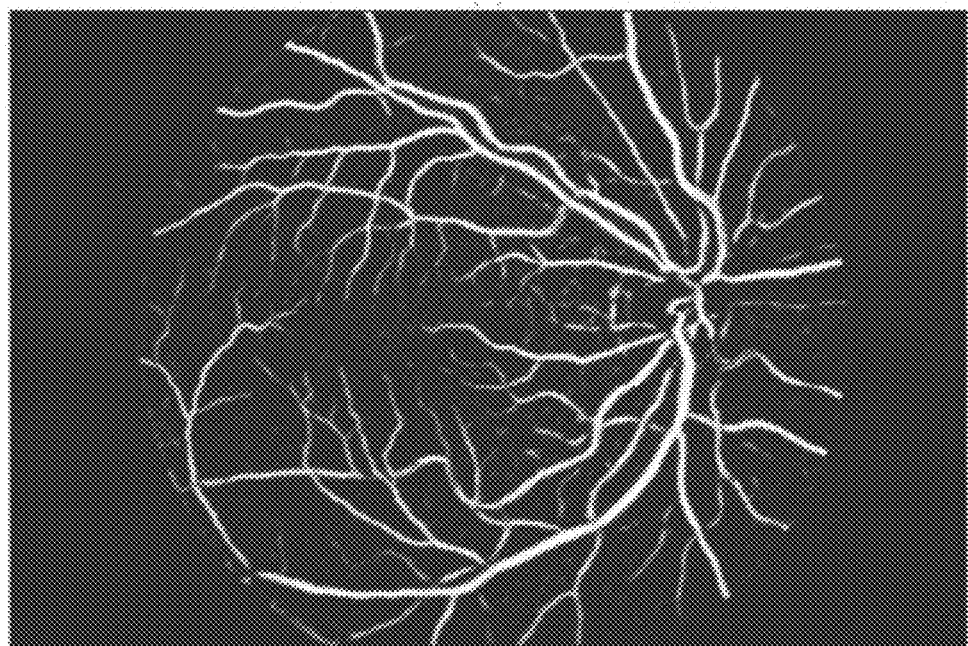
FIG. 5B shows the corresponding vesselness image of the color fundus image shown in FIG. 5A.
Figure 6A:
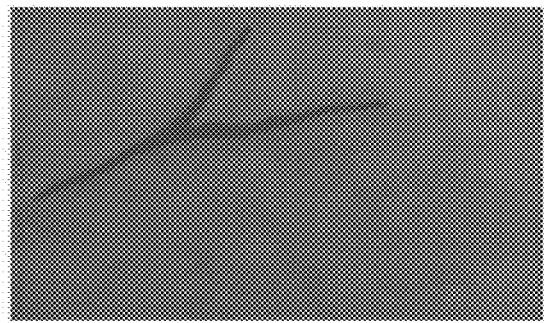
FIG. 6A shows a small segment of a vessel extracted from FIG. 5A or FIG. 5B.
Figure 6B:
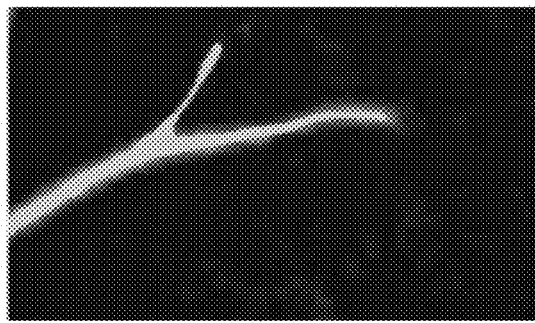
FIG. 6B shows a vessel probability image of FIG. 6A.
Figure 6C:
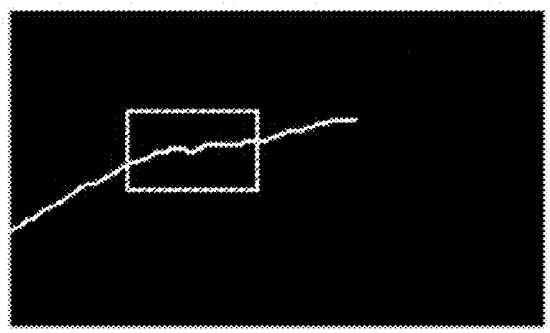
FIG. 6C shows a vessel centerline image of FIG. 6A.
Figure 6D:
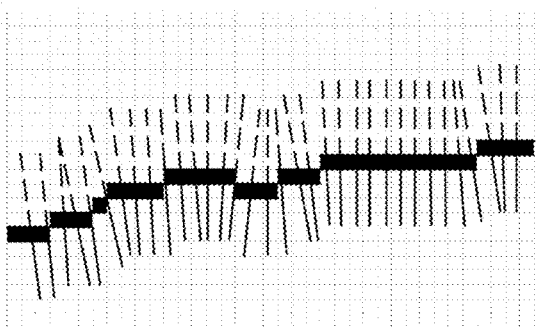
FIG. 6D shows vessel growing directions.
Figure 6E:
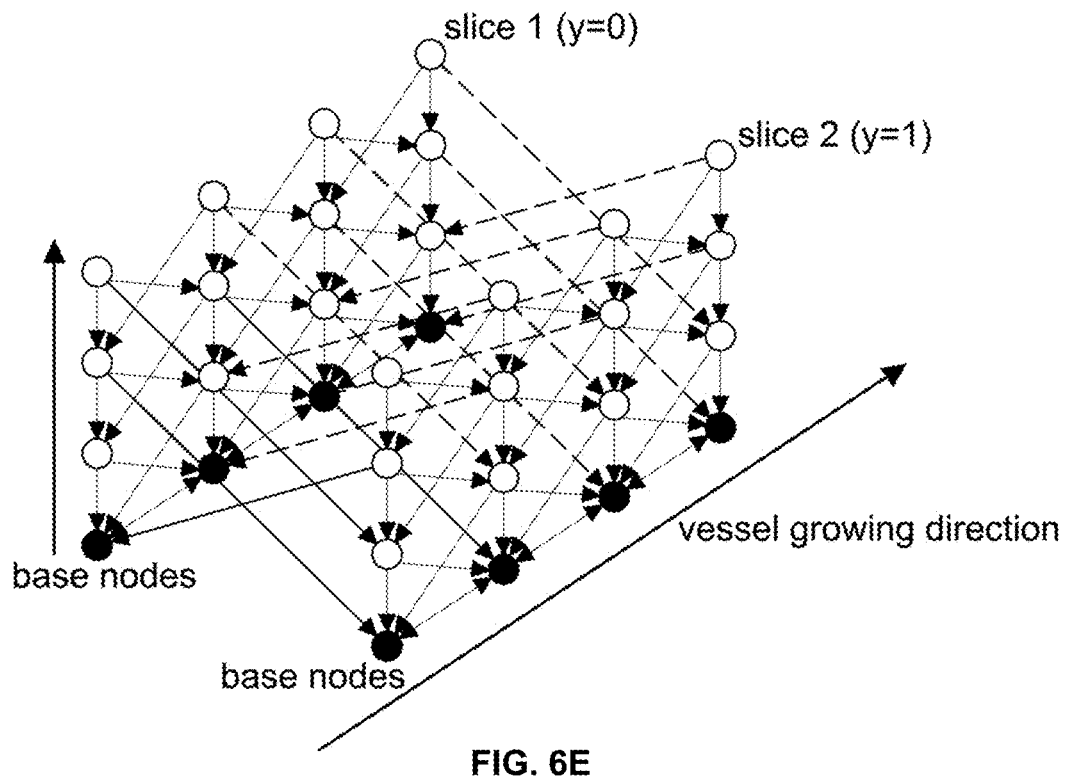
FIG. 6E shows a graph depiction of vessel growing directions.

An initial segmentation is needed to build the graph. The vesselness map can be used as the initial segmentation. One example image is shown in FIG. 5. FIG. 5a is a color fundus image. The white rectangular is enlarged and used for illustration in FIG. 6. FIG. 5b is the corresponding vesselness image. By thresholding the gray scale image, a binary vessel segmentation can be generated. A (constant) low threshold can be selected to better maintain the continuity of blood vessels. The trade-off is that small regions of noise may not be suppressed adequately. In order to solve this problem, the vessel regions with an area smaller than a pre-determined number (for example, 20) pixels can be erased from the thresholded image. A sequential thinning approach can then be applied to the binary vessel segmentation to find the vessel centerlines. In an alternative aspect, vessel width can be measured directly from the vesselness map. The vesselness image can be thresholded, generating a binary vessel segmentation. By way of example, a fixed threshold of 190 can be used. Widths can then be measured on this binary vessel map.

From the vessel centerline image, the bifurcation points and crossing points can be excluded. A bifurcation point can be defined as a centerline pixel with three eight-connected neighbors and a crossing point can be defined as a centerline pixel with four or more eight-connected neighbors. Hence, the vessel centerline image can be scanned first to get the centerline pixels that have three or more neighbors. By deleting the bifurcation points and crossing points, the vessel trees can be cut into vessel segments. From these vessel segments, the end points which have only one neighbor pixel can be found by scanning the image again. Starting from one end point, the vessel segment can be traced until the other end point is reached. In this way, all the vessel segments on the image are traced and labeled.

For each labeled vessel segment, the growing direction for every centerline pixel can be calculated. n adjacent centerline pixels can be used on both sides of the target centerline pixel and principal component analysis can be applied on the resulting vessel segment. The value of n can be a parameter of the image size, which is approximately 0.005 times the first dimension of the image size. For example, if the first dimension of an image is 600 pixels, the value of n would be three pixels, resulting in a total vessel segment length of seven pixels. In an aspect, the minimum value of n can be two. The first principal component can correspond to the growing direction of the pixel. An end point that does not have enough neighboring centerline pixels to define the vessel growing direction can be determined to have the direction of the nearest centerline pixel that has a definition of a vessel growing direction.

For the vessel growing direction, a counter-clockwise 90 degree is regarded as the normal direction for this point. Using the centerline pixels as the base nodes, profiles on the positive direction of the normals can be built as one slice and profiles on the negative direction can be built as another slice, as shown in FIG. 6.

FIG. 6 is an illustration of how to luxate the vessel normal profiles into a graph. FIG. 6a, a small segment of vessel extracted from FIG. 5. FIG. 6b, the vessel probability image of FIG. 6a. FIG. 6c, the vessel centerline image of FIG. 6a. FIG. 6d, the vessel growing directions are calculated and node normal profile perpendicular to the vessel growing direction are constructed. FIG. 6e, red normal profiles in FIG. 6d are used to build the red graph slice and the green normal profiles in FIG. 6d are used to build the green graph slice. The black nodes represent base nodes, corresponding to the black centerline pixels in FIG. 6d. Consequently, the red slice represents one boundary in FIG. 6d and the green slice represents the other boundary in FIG. 6d. Smoothness constraints (controlled by the arcs between adjacent columns) are applied differently to control the boundary smoothness within one boundary and between the two boundaries.

Along each normal profile Col (x, y) every node V (x, y, z)(z>0) has a directed arc to the node V(x, y, z−1). Along the x-direction, meaning along the same boundary, for each node, a directed arc is constructed from V (x, y, z) E Col (x, y) to V (x+1, y, max(0, z−$\Delta_x$))∈ Col (x+1, y). Similarly, arcs from V (x, y, z)∈ Col (x, y) to V (x−1, y, max(0, z−$\Delta_x$))∈ Col (x−1, y, z) are constructed. $\Delta_x$ is the maximum difference allowed between two adjacent normal profiles within one boundary. Along the y-direction, meaning between the two slices, arcs from V (x, y, z)∈ Col (x, y) to V (x, y+1, max (0, z−$\Delta_y$))∈ E Col (x, y+1, z) and arcs from V (x, y, z)∈ Col (x, y) to V (x, y−1, max (0, z−$\Delta_y$))∈ Col (x, y−1, z) are constructed. $\Delta_y$ is the maximum difference allowed between two corresponding normal profiles between the two boundaries. The base nodes are all connected. A surface is regarded feasible if it satisfies the smoothness constraint defined by $\Delta_x$ and $\Delta_y$. An optimal surface is defined as the surface with the minimum cost among all feasible surfaces defined in the 3-D volume.

Figure 7A:
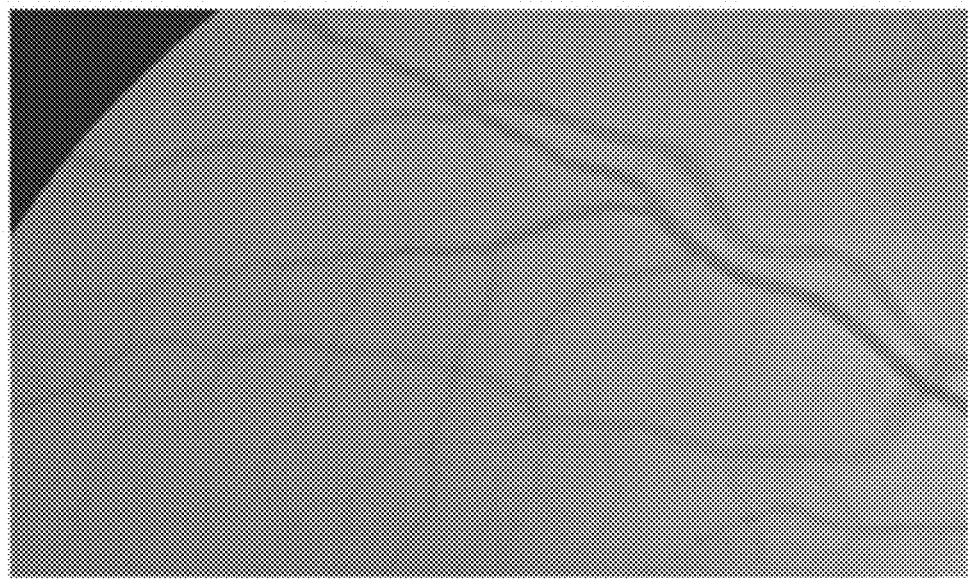
FIG. 7A shows an enlarged part of a channel image.
Figure 7B:
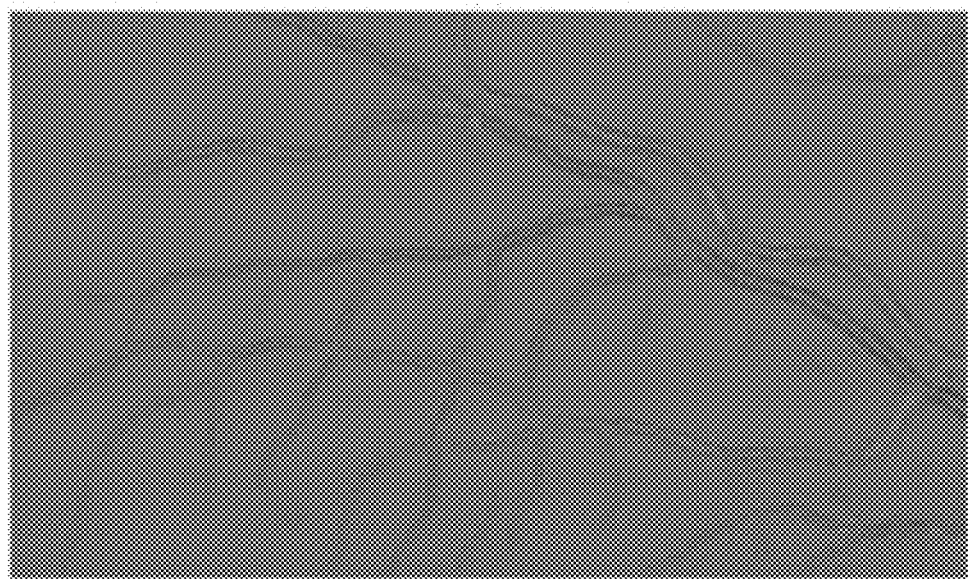
FIG. 7B shows an orientation sensitive 1D derivative of Gaussian result.

The cost image can be generated from the orientation sensitive 1D first order derivative of Gaussian of the green channel. The green channel of the color image usually shows the highest contrast between the blood vessels and background. In order to find the gradient of vessels specified at different locations with different orientations, a discrete convolution with the 1D derivative of Gaussian can be applied along the direction perpendicular to the vessel growing direction (as shown in FIG. 7). The derivative of Gaussian kernel is shown in Equation 1:

$$f(x; \sigma) = -\frac{x}{\sigma^3 \sqrt{2\pi}} \exp\left(-\frac{x^2}{2\sigma^2}\right), \qquad (1)$$

where σ is the only parameter in the first order derivative of Gaussian. FIG. 7 is an example. FIG. 7a shows an enlarged part of the green channel image. FIG. 7b shows the orientation sensitive 1D derivative of Gaussian result.

The value of $\Delta_x$ can be set to one to maintain the smoothness within one boundary and $\Delta_y$ can be set to two so that a difference is allowed between widths from the centerline to the left edge and from the centerline to the right edge, in case the centerline is not exactly at the center of the two edges. After the node-weighted directed graph is constructed, the optimal surface can be determined. To determine the vessel width, the coordinate difference between the two corresponding nodes on the optimal surface from the two slices can be calculated. To show the boundary on the image, the nearest integer coordinate of every node on the optimal surface can be calculated and shown on the image.

C. Classification into Arteries and Veins

To enable separate analysis of the arteries and the veins in the image, the previously detected vessel segments can be assigned to one of these two classes. In an aspect, a supervised system, i.e. trained with examples, can be used. After a training procedure, the classification method can be used to classify previously unseen centerline pixels into either artery or vein (AV classification). The pre-processing procedure and vessel width measurements can be applied to all images in the training set. An expert can indicate whether a given major vessel was an artery or vein for each of the training images.

In the training phase, a classifier can be trained using the expert labeled vessels in the training set in order to distinguish between both classes of centerline pixels. As not all vessels in the training set will be marked as artery or vein, centerline pixels from unmarked vessels are not included in the training dataset. For all remaining centerline pixels in the training images, a set of local features was extracted. Table I shows a list of exemplary extracted features that can be used. In general the features characterize the color as well as the color variation in the vessel. All features that are measured across the vessel can be measured on the profiles as previously determined.

TABLE 1

| Nr. | Feature description |
|---|---|
| 1-3 | Normalized Mean Hue, Saturation and Intensity across vessel. |
| 4-5 | Normalized Mean Red and Green plane intensities across the vessel. |
| 6-8 | Standard deviation of Hue, Saturation and Intensity across the vessel. |
| 9-10 | Standard deviation of Red and Green plane intensities across the vessel. |
| 11-13 | Normalized Hue, Saturation and Intensity under the centerline pixel. |
| 14-15 | Normalized Red and Green plane intensity under the centerline pixel. |
| 16-19 | Normalized highest and lowest intensity in the Red and Green plane across the vessel. |
| 20-27 | Intensity under the centerline pixel in a Gaussian blurred ($\sigma$ = 2, 4, 8, 16) version of the Red and Green plane. |

The absolute color of the blood in the vessels can vary between images and across subjects. This variation can have several causes. Primarily, the amount of hemoglobin oxygen saturation influences the reflectivity of the blood column, and this difference allows the difference between higher saturation arterial from lower saturation venous blood to be visualized. Next, lens absorption for different wavelengths is influenced by aging and the development of cataract, causing shifts in the spectral distribution of light reflected by blood. Individual difference in pigmentation of the retinal pigment epithelium below the blood vessels also influence the spectrum of reflected light. Finally, across examinations, even from the same subject, differences in flash intensity, flash spectrum, nonlinear optical distortions of the camera, flash artifacts, and focus also cause considerable variability. These factors complicate classification substantially, and normalization to zero mean and unit standard deviation of the vessel color features for every individual image can improve classification. After sampling the features for each centerline pixel, the appropriate labels can be assigned based on the reference standard and all training samples can be stored in a training dataset. This sampling process can be repeated for all images in the training set.

The training set can then be split into a separate classifier selection training and test set. Several different classifiers can be used, for example: k-Nearest Neighbor Classifier, Support Vector Machine Classifier, Linear Discriminant Classifier, or a Quadratic Discriminant Classifier. The classifier that maximizes the area under the Receiver Operator Characteristic (ROC) curve can be selected.

After the training phase is complete, the trained classifier can be applied to the images in the test set. All the test images can be preprocessed similarly to the training images. For each centerline pixel the complete set of 27 features was extracted, however fewer and/or different features can be used. The trained classifier can then be used to assign a soft label l, [0 . . . 1]. Here, a label close to 0 means the pixel was likely in an artery and a label close to 1 means a pixel was likely in a vein. It can be assumed that all pixels in a vessel segment are either in an artery or a vein. Each soft label assigned to a centerline pixel can be regarded as a vote for the label of the complete segment. Combining these votes can be done in many different ways including taking the median label for the entire vessel segment.

Due to variation in the local image characteristics, the soft labels assigned to each of the segments can vary over the image. A global threshold will not always successfully separate the arteries from the veins within a single subject and will vary between subjects. To perform the final classification the prior knowledge that arteries and veins usually come in pairs can be used. This means that, when going around the optic disc in a circle in region B of the ROI, one will generally encounter an artery after first encountering a vein and vice versa. Since this rule does not always hold and since finding the matching vessel segment for a particular different vessel segment is non-trivial, a voting procedure can be implemented.

During a voting procedure, all vessel segments intersecting with a circle of a certain diameter around the optic disc and within region B of the ROI can be eligible for matching. Finding the nearest neighbor vessel segment on a circle is straightforward and can be done by finding the nearest intersection point on the circle. The soft AV labels of both points can be compared and the vessel segment with the highest soft label can receive a vote for "vein" and the other can receive an "artery" vote. Then the next nearest unpaired vessel can be selected and the procedure repeated. The outcome of this procedure is dependent on the starting vessel segment. By picking a different vessel segment as the starting segment, the distribution of the AV votes amongst the vessel segments will vary. All vessel segments eligible for matching can therefore be selected once as the starting vessel and the matching procedure repeated. Finally, the votes can be counted and each of the vessel segments assigned a hard label (i.e. either artery or vein based on the received votes). Vessel segments with an equal number of artery and vein votes can be excluded from analysis.

D. Determining the AVR

In an aspect, the arteriolar-to-venular ratio can be defined as $$AVR = \frac{CRAE}{CRVE}$$

where CRAB is the Central Retinal Artery Equivalent and CRVE is the Central Retinal Vein Equivalent. To calculate these numbers, an iterative process for matching up vessels and calculating the CRAE and CRVE can be used. The widest 6 veins and arteries (these do not have to be paired) can be used although fewer total number of widths can be used in case not enough measurement points are available. Algorithm 1 shows an exemplary implementation.

---

Algorithm 1 The algorithm used to calculate the AVR

Input: Vector A of length |A| containing the widths of the found arteries and vector V of length |V| containing the widths of the found veins.
Output: The AVR.
Sort A and V in decreasing order and set the length of both vectors to min(|A|,|V|,6).
while |A| > 1 do
   Select and remove the first element f and last element l from A
   Store $\sqrt{(f^2 + l^2)} * 0.88$ in vector C
   if |A| equals 1 then
     Remove the last remaining element from A and store it in C
   end if
   A = C
   Sort A from large to small
end while
Clear C
while |V| > 1 do
   Select and remove the first element f and last element l from V
   Store $\sqrt{(f^2 + l^2)} * 0.95$ in vector C

```
Algorithm 1 The algorithm used to calculate the AVR if |V| equals 1 then
    Remove the last remaining element from V and store it in C
end if
V = C
Sort V from large to small
end while
Divide the remaining element in A by the remaining element in V to
obtain the final AVR.
```

In an aspect, the final voting procedure can be based on measurements obtained on a circle with a certain diameter. The chance that all vessel segments in the ROI will intersect with a circle of any particular diameter is small. Therefore, the voting procedure and AVR calculation should be repeated at various diameters within the AVR ROI (see FIG. 4). By way of example, the diameters can be from 1 DD to 1.5 DD in steps of 0.1 DD where DD was 360 pixels, so the voting and AVR calculation procedure can be repeated 6 times. Note that this samples the AVR ROI equidistantly. For each circle diameter, the AV voting procedure can be performed, the local vessel width can be measured and stored in two vectors, A for arteries and V for veins. Next, Algorithm 1 can be used to calculate the AVR. The resulting six AVR values can be averaged to arrive at the final AVR estimate for the complete image.

In an aspect, illustrated in FIG. 8, provided are methods and systems for automatic determination of arteriovenous ratio (AVR), comprising receiving an image at 801, detecting a region of interest in the image at 802, identifying arteries and veins in the region of interest at 803, determining vessel width measurements for the identified arteries and veins at 804, and estimating an arteriovenous ratio (AVR), from the vessel width measurements at 805. In an aspect, decreased AVR indicates higher propensity for a disease. For example, decreased from a "normal" AVR or decreased from a previous AVR. Thus, the methods and systems provide a novel quantitative approach to early detection of retinal and cardiovascular disease.

In an aspect, detecting a region of interest in the image can further comprise detecting an optic disc in the image. Identifying arteries and veins in the region of interest can comprise performing vessel segmentation on the image. Performing vessel segmentation on the image can further comprise utilizing a trained classifier to classify pixels in the image as artery or vein pixels.

In an aspect, the image can be one or more of, a color image, a multispectral image, an Optical Coherence Tomography image. The image can be of the retina, iris, skin, brain surface, or any tissue with visible blood vessels imaged using any two different wavelength imaging process.

The trained classifier can use a feature vector comprising one or more of, derivatives, texture, and color properties.

In an aspect, determining vessel width measurements for the identified arteries and veins comprises using one or more of, a graph search, a multiscale pixel feature based tobogganing method and splats. The graph search can use a multiscale cost function. The multiscale cost function can be derived from some combination of wavelet kernel lifting including Gabor, Gaussian derivative and Difference of Gaussians kernels.

The methods and systems provided can be applied to other two-dimensional blood vessel projections such as cardiac and brain angiograms.

In a further aspect, the methods and systems can be utilized to provide an indicator of disease propensity. The methods and systems can be applied to large quantities of images for batch processing and determination of a disease propensity for a group of persons.

In an aspect, provided are methods and systems to automatically determine artery/vein measures in an image region in an image. The methods and systems can utilize disc detection, disc centerpoint determination and disc diameter measurement to identify the image region. Pixel classification and mathematical morphology can be used to determine the artery/vein measures. The image can be a color image. The image can be a multispectral image. The image can be a combination of an OCT image and a multispectral image. The image can be of the retina, the iris, the skin, the brain surface, or of another tissue with visible blood vessels imaged using any two different wavelength imaging process.

In an aspect, the methods and systems can classify pixels in an image using artery and vein measurements. The classification can use a feature vector containing derivatives, texture and color properties. The color features can be normalized for each individual image. By way of example, a knn classifier or a support vector machine can be used to classify the pixels. The centerline of one or a plurality of vessels can be assigned a classification.

In a further aspect, provided are methods and systems to accurately measure local vessel parameters to supply features to the methods disclosed. In a further aspect, the methods and systems can measure local vessel texture patterns using filters. The filters can be, for example, Gaussian derivatives, Gabor filters or wavelet filters based filterbank, or a combination thereof. The filters can be obtained using image samples and a transform such as principal component analysis thereof.

In a still further aspect, provided are methods and systems to propagate pixel based artery vein classifications over the complete vessel to classify the entire vessels themselves. In a further aspect, provided are methods and systems to perform accurate width measurements of the retinal vessel between the boundaries of the vessel. The vessel boundaries can be determined using graph search. The graph search can use a multiscale cost function. The multiscale cost function can be derived from some combination of wavelet kernel lifting including Gabor, Gaussian derivative and Difference of Gaussians kernels. The boundaries can be determined using a multiscale pixel feature based tobogganing method and splats.

In an aspect, the methods and systems disclosed can analyze local vessel structure to determine how the vascular network is connected. In a further aspect, the methods and systems disclosed can determine the locations in the image where width measurements need to be obtained in order to calculate the AV-ratio. Disc detection, disc centerpoint determination and disc diameter measurement can be used to identify the image locations. The features can be normalized to all vessel pixels. The features can be normalized to all disc vessel pixels. The features can be normalized to all background pixels.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and systems. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

In a first experiment, sixty-five digital color fundus photographs were acquired for training and testing. All images were obtained from patients with primary open angle glaucoma at the University of Iowa Hospitals and Clinics using a 30° degree Zeiss fundus camera (Carl Zeiss Meditec, Dublin, CA), with digital back (OIS systems, Sacramento, CA). The images were centered on the disc. The dimensions of the images are 2392×2048 pixels with 8-bits per pixel per color plane, and stored in JPEG format for export. To train the AV classification component and determine the parameters for the algorithm, 25 digital color fundus photographs were randomly selected from the set of 65. The remaining 40 images were assigned to the test set and were only used to evaluate the complete system.

An ophthalmologist (AVD) labeled the major vessels in the images of the training set as either artery or vein to train the artery vein classification method. As only the vessel centerlines needed to be labeled, precise vessel segmentation was not needed. Labeling was done by manually drawing a line over the major vessels using a standard painting program. The colors blue and red were used for veins and arteries respectively.

Two components of the presented method were evaluated on the test images, the AV classification and the AVR determination. To evaluate the AV classification, the vessels in each of the images in the test set were manually labeled as either artery or vein by an ophthalmologist (AVD). In contrast to the way the major arteries and veins were labeled in the training set, only those parts of all vessels (i.e. including the small vessels) that were inside the AVR ROI were labeled in the test set. The expert labeled all vessels in the ROI as either an artery or a vein.

To set the AVR reference standard, a semi-automated computer program developed by the University of Wisconsin in Madison, WI, USA was used (IVAN). Two ophthalmologists processed the images in the test set using this software. Both ophthalmologists were instructed in the use of the software using the protocols defined by the software developers. IVAN is semi-automated; the AVR ROI localization, the vessel width measurements and the artery vein classification require manual adjustment. On average a human observer takes around 10 minutes per image to perform the analysis. The software is capable of producing several different AVR measures. The ratios obtained by the first ophthalmologist (MDA) were used as the reference standard and the second ophthalmologist's (AVD) ratios were used to determine the variability between experts.

The methods and systems provided herein were applied to all 40 test images. The system was able to find the optic disc and successfully placed the AVR in all 40 images. This was verified by visual inspection and the AVR ROI was centered on the optic disc in all 40 images.

Figure 9:
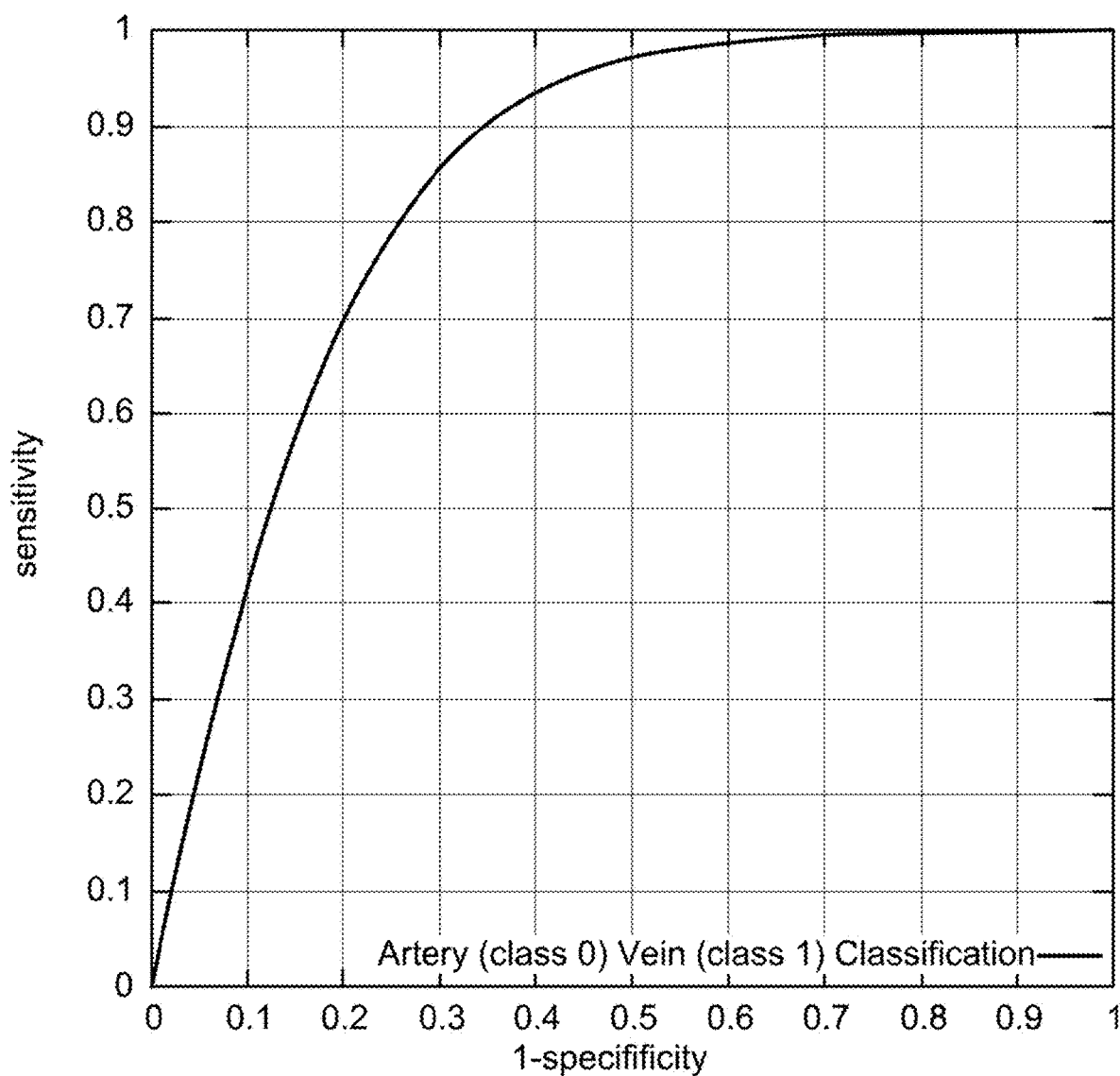
FIG. 9 shows a curve from a ROC analysis.

To compare the artery/vein classification with the labeling by the human expert we performed an ROC analysis with class 0 being artery and class 1 being vein. Note that this analysis was performed on the vessel centerline pixels only. The proposed classification system assigned each centerline pixel a likelihood value that it was inside of a vein. That is, a value of 0 indicates a centerline pixel likely inside an artery and a value of 1 indicates a centerline pixel likely in a vein. A ROC analysis was performed and the resulting curve is shown in FIG. 9. The system attained an area under the curve of 0.84. This means that, given a randomly selected artery pixel and a randomly selected vein pixel, in 84% of cases the automatic system will correctly assign a higher likelihood to the vein centerline pixel.

Figures 10A, 10B:
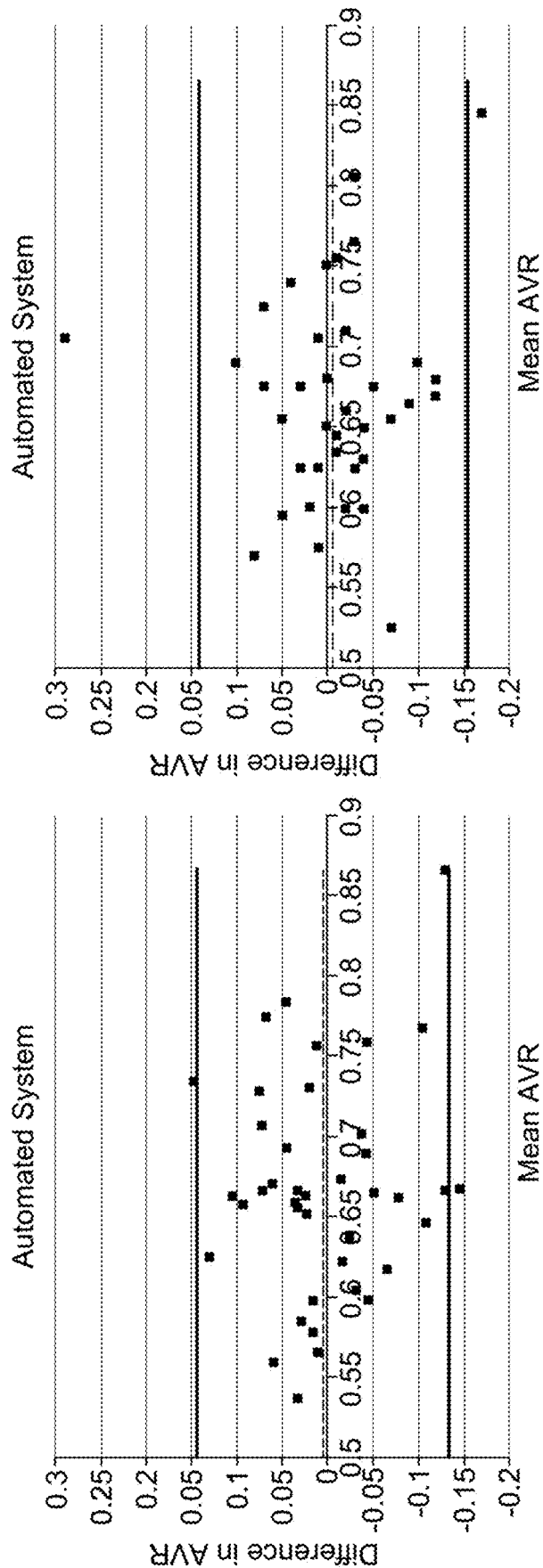
FIG. 10A provides Bland-Altman plots or the agreement between an automatic system and a reference standard.
FIG. 10B provides Bland-Altman plots or the agreement between a second observer and the reference standard.

To evaluate the ability of the system to assign an artery vein ratio to an image the AVRs as produced by the system and the second observer were directly compared with the reference standard. Paired t-test showed that there was no significant difference between the reference standard and the system's measurements (p=0.66). The same holds for the second observer's measurements (p=0.59). Table 2 shows the results for the individual image. The "Reference" column contains the reference standard for reading, "System" is the output from the automatic system, and "Obs. 2" contains the reading from the second observer. All number in italics represent differences between the first and second. To visually asses the agreement between both the automatic system and the second observer and the reference standard the results are plotted in Bland-Altman plots in FIG. 10. This graph plots the mean of two AVR measurements against the difference between them and allows a visual assessment of the distribution of errors and the agreement between the two methods. FIG. 10 provides the Bland-Altman plots or the agreement between the automatic system and the reference standard FIG. 10a and between the second observer and the reference standard FIG. 10b. The red lines represent the 95% limits or agreement. The dotted line represents the mean difference between AVR measurements.

TABLE 2

| Image | Reference | System | Error | Obs. 2 | Error |
|---|---|---|---|---|---|
| 1 | 0.70 | 0.62 | 0.08 | 0.71 | 0.01 |
| 2 | 0.76 | 0.81 | 0.05 | 0.75 | 0.01 |
| 3 | 0.66 | 0.81 | 0.15 | 0.69 | 0.03 |
| 4 | 0.75 | 0.76 | 0.01 | 0.75 | 0.00 |
| 5 | 0.53 | 0.59 | 0.06 | 0.61 | 0.08 |
| 6 | 0.93 | 0.80 | 0.13 | 0.76 | 0.17 |
| 7 | 0.63 | 0.70 | 0.07 | 0.68 | 0.05 |
| 8 | 0.70 | 0.59 | 0.11 | 0.65 | 0.05 |
| 9 | 0.65 | 0.68 | 0.03 | 0.64 | 0.01 |
| 10 | 0.78 | 0.74 | 0.04 | 0.75 | 0.03 |
| 11 | 0.65 | 0.58 | 0.07 | 0.65 | 0.00 |
| 12 | 0.67 | 0.74 | 0.07 | 0.65 | 0.02 |
| 13 | 0.64 | 0.68 | 0.04 | 0.71 | 0.07 |
| 14 | 0.69 | 0.77 | 0.08 | 0.76 | 0.07 |
| 15 | 0.56 | 0.57 | 0.01 | 0.85 | 0.29 |
| 16 | 0.64 | 0.70 | 0.06 | 0.74 | 0.10 |
| 17 | 0.57 | 0.60 | 0.03 | 0.62 | 0.05 |
| 18 | 0.62 | 0.59 | 0.03 | 0.58 | 0.04 |
| 19 | 0.64 | 0.67 | 0.03 | 0.61 | 0.03 |
| 20 | 0.68 | 0.67 | 0.01 | 0.68 | 0.00 |
| 21 | 0.52 | 0.55 | 0.03 | 0.45 | 0.07 |
| 22 | 0.62 | 0.58 | 0.04 | 0.63 | 0.01 |
| 23 | 0.67 | 0.71 | 0.04 | 0.63 | 0.04 |
| 24 | 0.71 | 0.67 | 0.04 | 0.62 | 0.09 |
| 25 | 0.57 | 0.59 | 0.02 | 0.58 | 0.01 |
| 26 | 0.72 | 0.74 | 0.02 | 0.76 | 0.04 |
| 27 | 0.65 | 0.63 | 0.02 | 0.64 | 0.01 |
| 28 | 0.56 | 0.69 | 0.13 | 0.49 | 0.07 |
| 29 | 0.73 | 0.60 | 0.13 | 0.61 | 0.12 |
| 30 | 0.64 | 0.66 | 0.02 | 0.63 | 0.01 |
| 31 | 0.63 | 0.61 | 0.02 | 0.68 | 0.05 |
| 32 | 0.72 | 0.68 | 0.04 | 0.70 | 0.02 |
| 33 | 0.59 | 0.61 | 0.02 | 0.61 | 0.02 |
| 34 | 0.61 | 0.71 | 0.10 | 0.59 | 0.02 |
| 35 | 0.65 | 0.68 | 0.03 | 0.61 | 0.04 |
| 36 | 0.74 | 0.59 | 0.15 | 0.64 | 0.10 |
| 37 | 0.69 | 0.64 | 0.05 | 0.62 | 0.07 |
| 38 | 0.82 | 0.72 | 0.10 | 0.79 | 0.03 |
| 39 | 0.61 | 0.70 | 0.09 | 0.64 | 0.03 |
| 40 | 0.74 | 0.81 | 0.07 | 0.62 | 0.12 |
| mean | 0.67 | 0.67 | 0.06 | 0.66 | 0.05 |
| SD | 0.08 | 0.07 | 0.04 | 0.08 | 0.05 |
| min | 0.52 | 0.55 | 0.01 | 0.45 | 0.00 |
| max | 0.93 | 0.81 | 0.15 | 0.85 | 0.29 |

This study showed that a completely automatic method can estimate the AVR in retinal color images with a mean error similar to that of a human expert who was using the reference standard system IVAN. The automatic method also successfully classified retinal vessel pixels into being part of an artery or vein.

Compared to previously presented methods the area under the ROC curve for the AV classification may not seem an improvement. However, it is important to note that, in contrast with previously presented methods, all detected vessel centerline pixels inside region B of the ROI were classified. This includes vessels for which the observers were not able to see whether they were an artery or a vein without tracing the vessel back to its source. The prior methods have used clustering instead of classification to overcome the challenges presented by the high variability between fundus images. The use of color features that are normalized for each individual image, combined with a supervised classification approach, leads to better results than using clustering.

Table 2 shows the error with respect to the reference standard of the automated system for each image. The mean AVR values and their standard deviations of the reference standard are very close between the automated system and observer 2, a statistical test showed there was no significant difference between the means. Nevertheless, there are 8 AVR measurements by the automated system that have an error above 0.10 when compared with the reference standard. However, of these, 5 show a relatively good agreement with the measurement done by the second observer. The Bland-Altman plots (see FIG. 10) show that both the automated system and the second observer have no bias as the mean difference between the AVR measurements is close to 0. The 95% limits of agreement for both the automated and second observer are also almost the same. However, the second observer has two large outliers without which the 95% limits of agreement would have moved somewhat closer to 0.

In a second experiment, to evaluate our method further, the relationship between the average vessel width (both arteries and veins) and the distance to the optic disc was determined in a sample of 600 composite color fundus images, each consisting of two registered and blended fundus images.

The REVIEW database was used to validate the correctness of the methods and systems. Each profile in the REVIEW database consists of 15 numbers: series number, image number, segment number and four data for each of three observers. The three observers are denoted as $O_1$, $O_2$ and $O_3$. For each observer, there are four measurements for two points on each edge ($x_1$, $y_1$, $x_2$ and $y_2$). The vessel centerline is defined as $(x_1-x_2)^2+(y_1-y_1)^2$ and the vessel width as $(x_1-x_2)^2+(y_1-y_2)^2$ for each observer (http://ReviewDB.lincoln.ac.uk). A reference standard, denoted by RS, is then created by averaging the manual results of the three observers.

The vessel centerlines were determined as described herein and mapped to the centerlines in the RS, so that only those vessel centerline pixels were analyzed that also occurred in the RS. Otherwise the centerline pixel was labeled as absent.

The methods and systems described herein were compared with the results of prior methods, where 1DG and 2DG mean 1-D Gaussian model-fitting and 2-D Gaussian model-fitting, respectively.

To determine this relationship on the dataset of 600 registered fundus images the vessel widths of all vessels was obtained as described herein. Circular regions of interest one pixel wide were centered on the optic disc center. The average width of all vessels in each region of interest (i.e. both arteries and veins) was then plotted in a graph, as well as the 95% confidence interval (CI) of the average width. Centerline pixels with a distance larger than 450 pixels from the disc were too close to the edge of the image—less than 2.1% of all centerline pixels—and were eliminated from further analysis.

Figure 11A:
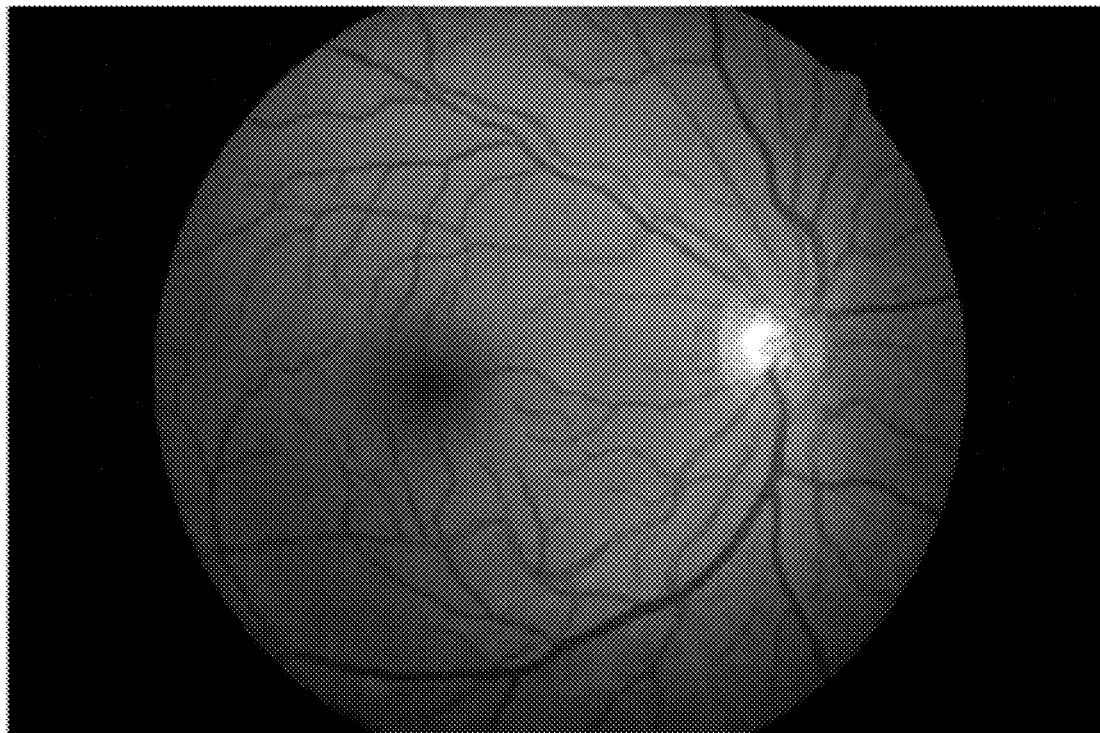
FIG. 11A shows an image from the CLRIS database.
Figure 11B:
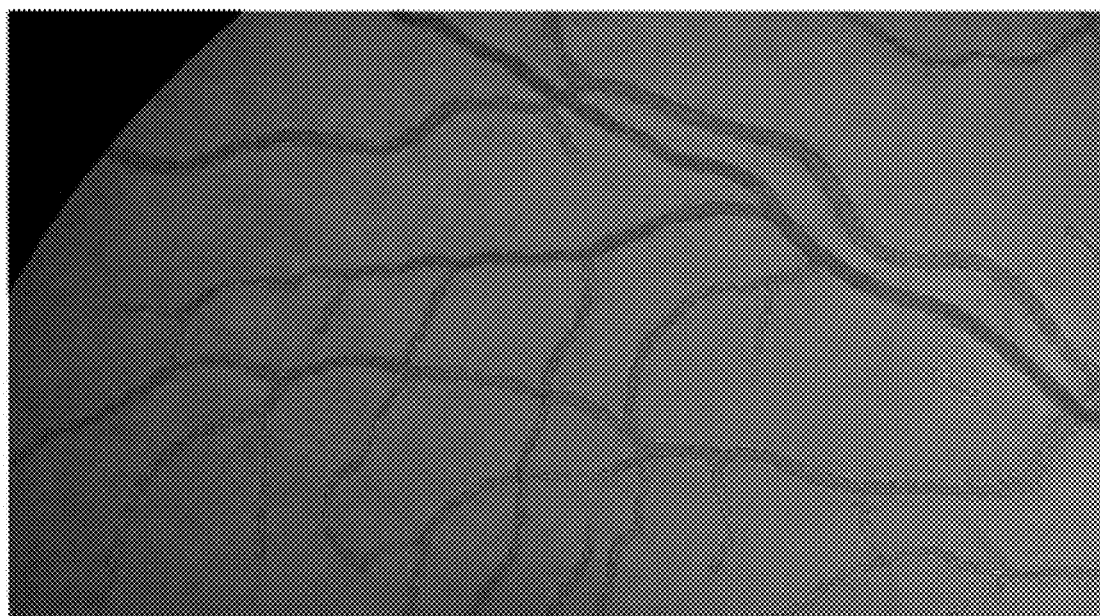
FIG. 11B shows an enlarged part of the image shown in FIG. 11A.

An example of the quality of the obtained vessel boundary detection is shown in FIG. 11. Good performance is obtained on even the smallest vessels, which have low contrast. FIG. 11a is one image from the CLRIS database. Image size is 2160×1440, a=4. FIG. 11b is an enlarged part of image FIG. 11a.

The methods and systems provided herein were compared to other known algorithms in Table 3 to Table 6. The first three rows are the manual result from the observers. Rows 4-8 show the results of the other algorithms. The last row shows the result of the presently disclosed methods and systems. The first column is the success rate. Every centerline pixel that had corresponding ground truth profiles as a "success measurement", irrespective of the estimate of the width. Therefore all measurements with a corresponding ground truth profile were included even if the measurements did not result in a meaningful estimation. The columns 2-3 are the mean and standard deviation of all measurements labeled as 'success measurement'. Columns 4-5 are the signed mean and standard deviation of the point-by-point differences.

TABLE 3

VESSEL WIDTH MEASUREMENT ACCURACY OF HRIS
(SUCCESS RATE IN PERCENTAGE, MEAN μ AND
STANDARD DEVIATION σ IN PIXEL)

| Method Name | Success Rate % | Measurement μ | σ | Difference μ | σ |
|---|---|---|---|---|---|
| Observer 1 ($O_1$) | 100 | 4.12 | 1.25 | −0.23 | 0.288 |
| Observer 2 ($O_2$) | 100 | 4.35 | 1.35 | 0.002 | 0.256 |
| Observer 3 ($O_3$) | 100 | 4.58 | 1.26 | 0.23 | 0.285 |
| Gregson's Algorithm | 100 | 7.64 | — | 3.29 | 2.841 |
| Half-height full-width (HHFW) | 88.3 | 4.97 | — | 0.62 | 0.926 |
| 1-D Gaussian Model-fitting | 99.6 | 3.81 | — | −0.54 | 4.137 |
| 2-D Gaussian Model-fitting | 98.9 | 4.18 | — | −0.17 | 6.019 |
| Extraction of Segment Profiles (ESP) | 99.7 | 4.63 | — | 0.28 | 0.42 |
| Proposed Method | 100 | 4.56 | 1.30 | 0.21 | 0.567 |

TABLE 4

VESSEL WIDTH MEASUREMENT ACCURACY OF CLRIS
(SUCCESS RATE IN PERCENTAGE, MEAN μ AND
STANDARD DEVIATION σ IN PIXEL)

| Method Name | Success Rate % | Measurement μ | σ | Difference μ | σ |
|---|---|---|---|---|---|
| Observer 1 ($O_1$) | 100 | 13.19 | 4.01 | −0.61 | 0.566 |
| Observer 2 ($O_2$) | 100 | 13.69 | 4.22 | −0.11 | 0.698 |
| Observer 3 ($O_3$) | 100 | 14.52 | 4.26 | 0.72 | 0.566 |
| Gregson's Algorithm | 100 | 12.8 | — | −1.0 | 2.841 |
| Half-height full-width (HHFW) | 0 | — | — | — | — |

TABLE 4-continued

VESSEL WIDTH MEASUREMENT ACCURACY OF CLRIS
(SUCCESS RATE IN PERCENTAGE, MEAN μ AND
STANDARD DEVIATION σ IN PIXEL)

| Method Name | Success Rate % | Measurement μ | Measurement σ | Difference μ | Difference σ |
|---|---|---|---|---|---|
| 1-D Gaussian Model-fitting | 98.6 | 6.3 | — | −7.5 | 4.137 |
| 2-D Gaussian Model-fitting | 26.7 | 7.0 | — | −6.8 | 6.019 |
| Extraction of Segment Profiles (ESP) | 93.0 | 15.7 | — | −1.90 | 1.469 |
| Proposed Method | 94.1 | 14.05 | 4.47 | 0.08 | 1.78 |

TABLE 5

VESSEL WIDTH MEASUREMENT ACCURACY OF VDIS
(SUCCESS RATE IN PERCENTAGE, MEAN μ AND
STANDARD DEVIATION σ IN PIXEL)

| Method Name | Success Rate % | Measurement μ | Measurement σ | Difference μ | Difference σ |
|---|---|---|---|---|---|
| Observer 1 ($O_1$) | 100 | 8.50 | 2.54 | −0.35 | 0.543 |
| Observer 2 ($O_2$) | 100 | 8.91 | 2.69 | 0.06 | 0.621 |
| Observer 3 ($O_3$) | 100 | 9.15 | 2.67 | 0.30 | 0.669 |
| Gregson's Algorithm | 100 | 10.07 | — | 1.22 | 1.494 |
| Half-height full-width (HHFW) | 78.4 | 7.94 | — | −0.91 | 0.879 |
| 1-D Gaussian Model-fitting | 99.9 | 5.78 | — | −3.07 | 2.110 |
| 2-D Gaussian Model-fitting | 77.2 | 6.59 | — | −2.26 | 1.328 |
| Extraction of Segment Profiles (ESP) | 99.6 | 8.80 | — | −0.05 | 0.766 |
| Proposed Method | 96.0 | 8.35 | 3.00 | −0.53 | 1.43 |

TABLE 6

VESSEL WIDTH MEASUREMENT ACCURACY OF KPIS
(SUCCESS RATE IN PERCENTAGE, MEAN μ AND
STANDARD DEVIATION σ IN PIXEL)

| Method Name | Success Rate % | Measurement μ | Measurement σ | Difference μ | Difference σ |
|---|---|---|---|---|---|
| Observer 1 ($O_1$) | 100 | 7.97 | 0.47 | 0.45 | 0.234 |
| Observer 2 ($O_2$) | 100 | 7.60 | 0.42 | 0.08 | 0.213 |
| Observer 3 ($O_3$) | 100 | 7.00 | 0.52 | −0.52 | 0.233 |
| Gregson's Algorithm | 100 | 7.29 | — | −0.23 | 0.602 |
| Half-height full-width (HHFW) | 96.3 | 6.47 | — | −1.05 | 0.389 |
| 1-D Gaussian Model-fitting | 100 | 4.95 | — | −2.57 | 0.399 |
| 2-D Gaussian Model-fitting | 100 | 5.87 | — | −1.65 | 0.337 |
| Extraction of Segment Profiles (ESP) | 100 | 6.56 | — | −0.96 | 0.328 |
| Proposed Method | 99.4 | 6.38 | 0.59 | −1.14 | 0.67 |

Among the four datasets, the HRIS dataset has the highest image resolution (3584×2438 pixels). The performance of the vessel width detection is comparable to the observers.

The CLRIS dataset images have a resolution of 2160×1440 pixels. The mean vessel with and the point-by-point difference mean are very close to the observers' performance. But the point-by-point difference standard deviation is high. The VDIS dataset has a resolution of 1360×1024 pixels. The mean vessel width is 0.53 pixels smaller than the ground truth. The KPIS dataset has the smallest image resolution, 288×119 pixels and 170×92 pixels.

Testing indicates that fundus images with a higher resolution can be measured more accurately with a larger σ. The final choice of a is σ=7 for HRIS dataset, σ=4 for CLRIS and VDIS, σ=1 for KPIS.

Figure 12:
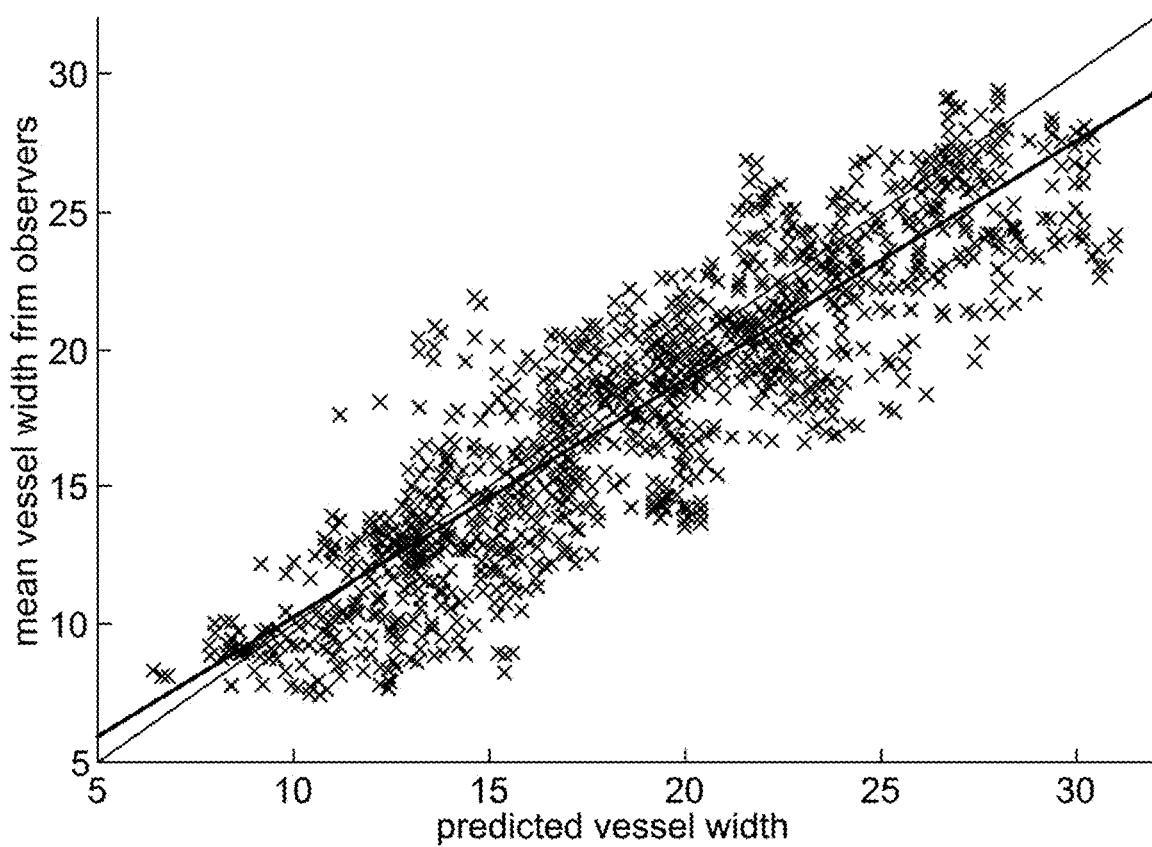
FIG. 12 shows a correlation of predicted vessel width and a mean of the observers' measurement for HRIS.

FIG. 12 shows the correlation of predicted vessel width and the mean of the observers' measurement for HRIS. The regression line shows the prediction tends to give a smaller measurement for vessels with fine vessels while a larger measurement for large vessels, compared to the observers' measurements. Each point represent one profile. The red line is the y=x line. The black line is the regression line (y=0.87x+1.56).

Figure 13:
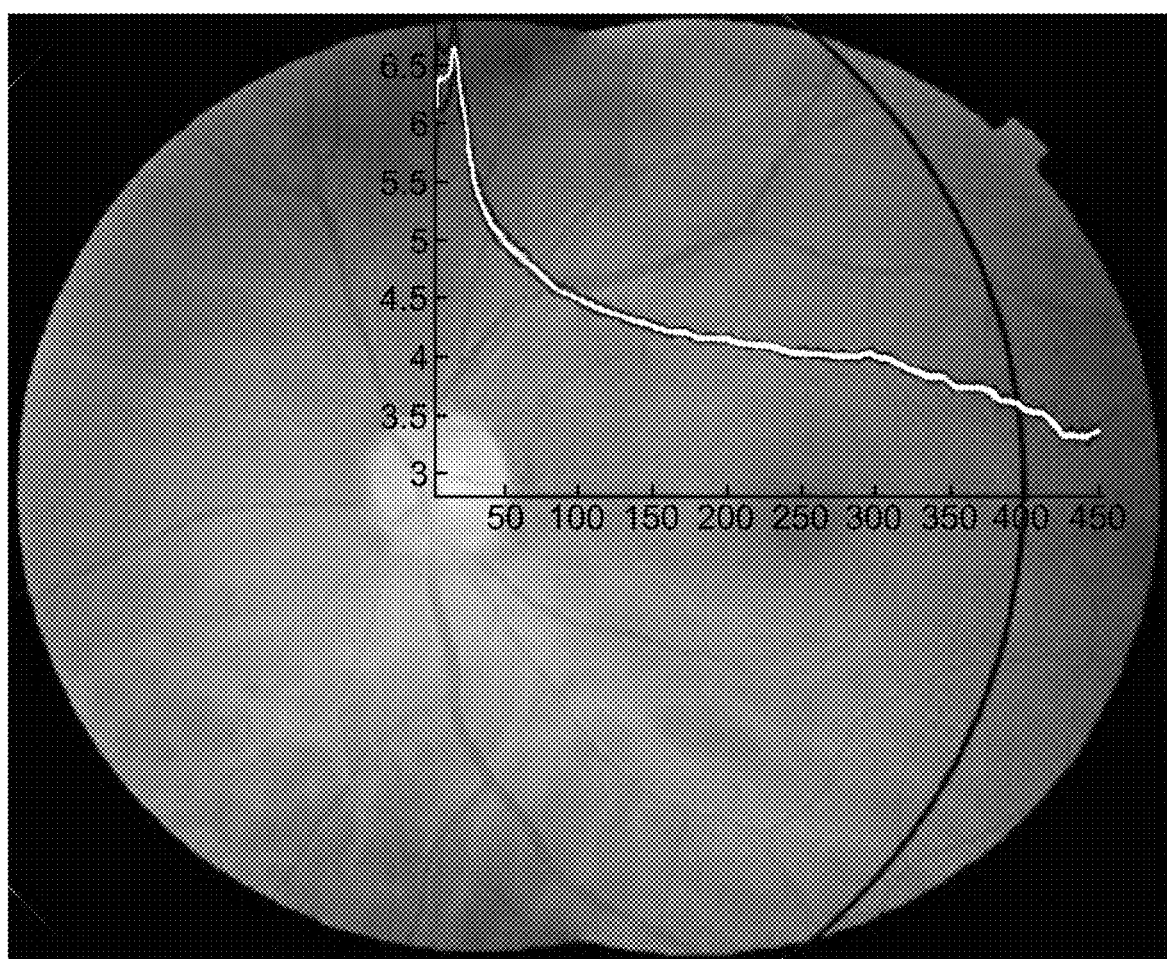
FIG. 13 illustrates a relationship between vessel width and distance to optic disc.

The relationship between vessel width and distance from the optic disc center is shown in FIG. 13. A total of 2,936,749 center line pixels were extracted from the 600 images. If the pixels near the center of optic disc are not considered, where the blood vessels show a very complicated structure, the average vessel width shows a monotonic decrease from a distance of 20 pixels to 450 pixels, with a sudden slope change at a distance of 300 pixels to the optic disc. For vessels near the optic disc border, the average vessel width is about 5.0 pixels (approximately 75 microns) while the vessels that have a distance of 450 pixels to the optic disc have an average vessel width of 3.5 pixels (approximately 52.5 microns).

FIG. 13 illustrates relationship between vessel width and distance to optic disc. The black circle marks a 400 pixels to the optic disc center. The vessel width analysis starts from the optic disc center and ends at a distance of 450 pixels (the x-axis). The y-axis shows the vessel width in pixels. The green line is the average vessel width. The black lines are the 95% confidence interval lines. Image resolution is about 800×700 pixels. Scale parameter (J=4 pixels was used.

The methods and systems provided can identify the retinal blood vessel boundaries using a graph-based approach. The results of the evaluation show that the blood vessel boundaries are accurate, and that the methods and systems outperform the prior algorithm on two datasets of standard retinal image resolution. The presently disclosed methods and systems allow for the identification of retinal vessel boundaries of even small vessels on standard posterior pole images as used in diabetic retinopathy screening programs around the world.

The results indicate that the relationship between vessel width with distance and the optic disc center is inverse and monotonous. Using this method, the relationship between the average retinal vessel diameter and the distance from the optic disc from 600 patients with diabetes was reliably determined. Except for the vessel pixels near the center of the optic disc (about 20 pixels), the blood vessel width shows a monotonic decrease considering the distance from the optic disc to the center. This is most likely caused by branching—if it is assumed that the blood vessel volume to be unchanged. If the number of blood vessels is kept constant, the higher the branch frequency with increasing distance to the optic disc the larger the slope of the width decrease. At a distance of around 300 pixels, there is a slight slope change in average vessel width, most likely caused by the fact that this is where the image centered on the optic disc ends and transitions to the fovea centered image that is registered to it in our dataset.

Figure 14A:
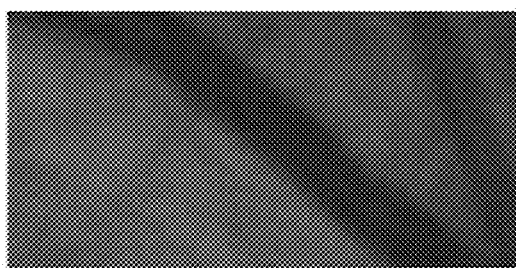
FIG. 14A shows a test vessel segment from HRIS
Figure 14B:
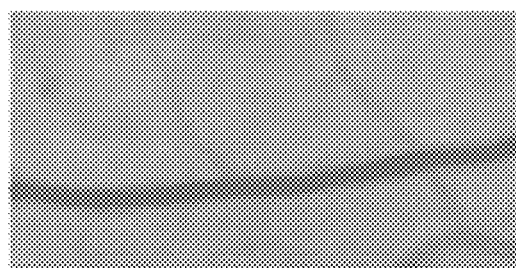
FIG. 14B shows a test vessel segment from KPIS.
Figure 14C:
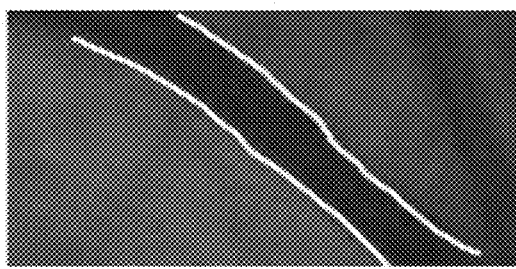
FIG. 14C shows the vessel width measurement result of FIG. 14A.
Figure 14D:
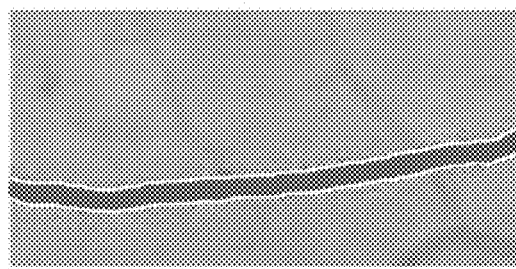
FIG. 14D shows the vessel width measurement result of FIG. 14B.
Figure 14E:
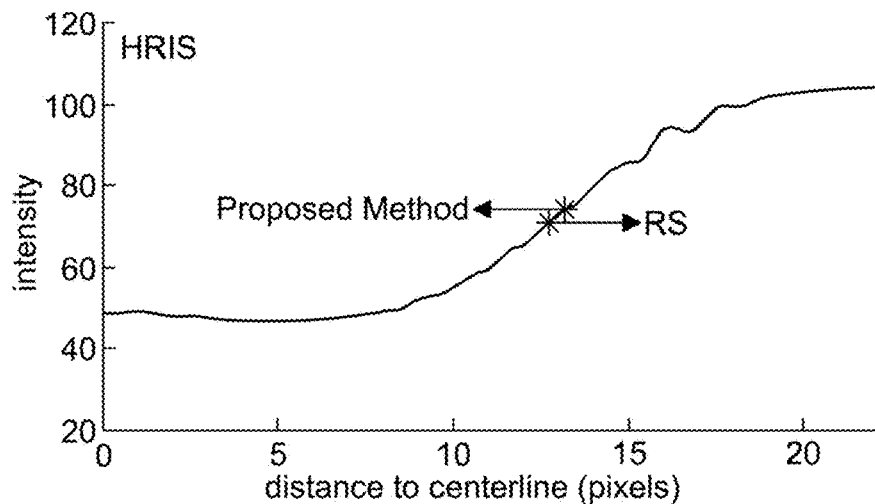
FIG. 14E shows the cross-sectional view of vessel intensity with regard to the distance to the centerline for FIG. 14A.
Figure 14F:
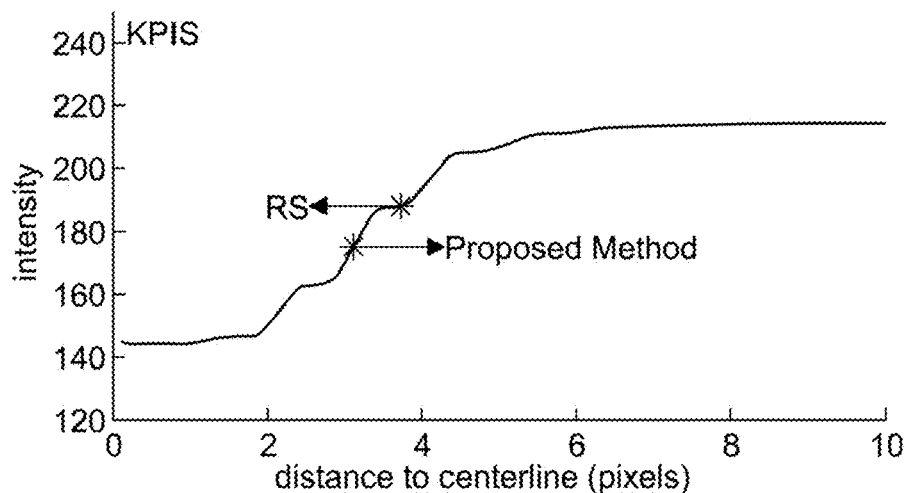
FIG. 14F shows a cross-sectional view of vessel intensity with regard to a distance to a centerline of the test vessel segment shown in FIG. 14B.

FIG. 14 illustrates vessel width measurement on vessel segments with different resolutions, FIG. 14a, one test vessel segment from HRIS. The length of the vessel segment is 173 pixels. FIG. 14b one test vessel segment from KPIS. The length of the vessel segment is 226 pixels. FIG. 14c the vessel width measurement result of (a). If the detected edge is not at an integer location, the nearest integer coordinate is shown. FIG. 14d the vessel width measurement result of (b). If the detected edge is not at an integer location, the nearest integer coordinate is shown. FIG. 14e the cross-sectional view of vessel intensity with regard to the distance to the centerline for (a). The black curve is the average of 173 normal profiles in the vessel segment. Intensities at non-integer locations are linearly interpolated. The red star is the average vessel width across the whole vessel segment marked by observers. The green star is the average vessel width across the whole vessel segment measured by proposed method. The two boundaries are flipped and shown in one figure. FIG. 14f the cross-sectional view of vessel intensity with regard to the distance to the centerline for FIG. 14b. The black curve is the average of 226 normal profiles in the vessel segment. Intensities at non-integer locations are linearly interpolated. The red star is the average vessel width across the whole vessel segment marked by observers. The green star is the average vessel width across the whole vessel segment measured by proposed method. The two boundaries are flipped and shown in one figure.

The methods provided have high computational performance. For a retinal image of size 2160×1440 pixels, vesselness map creation takes about 110 seconds, and this is an operation O(n), where n is the number of pixels. The image skeletonization and small region removal takes about 120 seconds, and this is also an operation i(n). The total number of centerline pixels is around 20000 pixels (or 0.0064n) and the total number of vessel segments is 160. Consequently the average length of the graph is around 125 pixels. The average size of the graph would be slice number x height of graph x length of graph, which is 45000 (or 0.0145n) in this case. It takes around 9 seconds to build all the graphs in the image. The method we used to solve the max-flow problem is a pseudoflow algorithm. The running time is $O(n^3)$ [23]. It takes about 41 seconds to solve all the graphs in the example image.

The method and systems provided for retinal vessel boundary detection based on graph search have been validated it on a publicly available dataset of expert annotated vessel widths. An advantage is in the detection of both boundaries simultaneously, and is therefore more robust than methods which detect the boundaries one at a time. The simultaneous detection of both borders makes the accurate detection possible even if one boundary is of low contrast or blurred. Overall, the method is robust as the only algorithmic parameter is σ in the cost function, and the final measurement is insensitive to the choice of σ.

One skilled in the art will appreciate that provided is a functional description and that the respective functions can be performed by software, hardware, or a combination of software and hardware. In one exemplary aspect, the methods and systems can comprise a computer 1501 as illustrated in FIG. 15 and described below.

Figure 15:
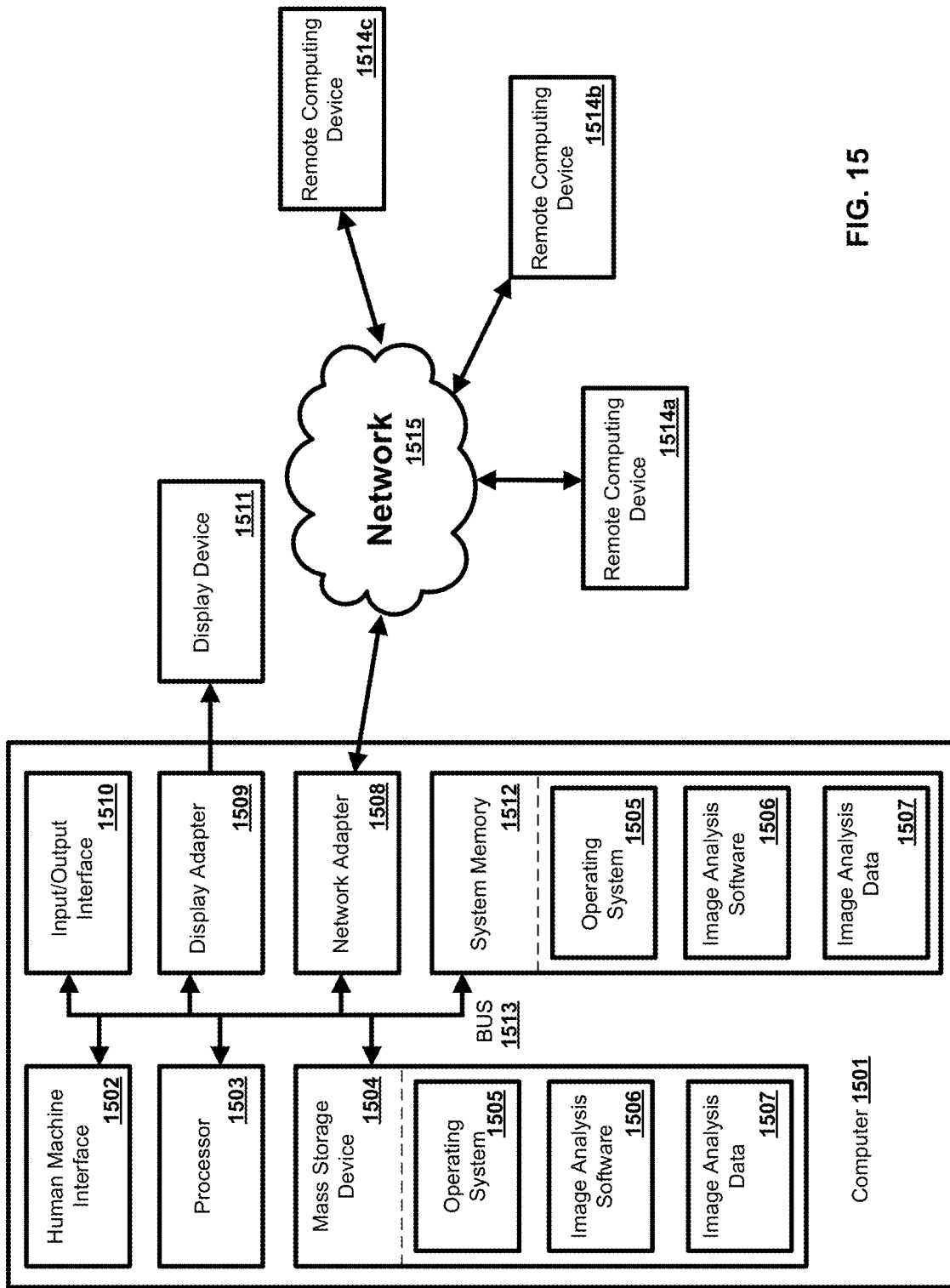
FIG. 15 is an exemplary operating environment.

FIG. 15 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 1501. The components of the computer 1501 can comprise, but are not limited to, one or more processors or processing units 1503, a system memory 1512, and a system bus 1513 that couples various system components including the processor 1503 to the system memory 1512. In the case of multiple processing units 1503, the system can utilize parallel computing.

The system bus 1513 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 1513, and all buses specified in this description can also be implemented over a wired or wireless network connection and each of the subsystems, including the processor 1503, a mass storage device 1504, an operating system 1505, image analysis software 1506, image analysis data 1507, a network adapter 1508, system memory 1512, an Input/Output Interface 1510, a display adapter 1509, a display device 1511, and a human machine interface 1502, can be contained within one or more remote computing devices 1514a,b,c at physically separate locations, connected through buses of this form, in effect implementing a fully distributed system.

The computer 1501 typically comprises a variety of computer readable media. Exemplary readable media can be any available media that is accessible by the computer 1501 and comprises, for example and not meant to be limiting, both volatile and non-volatile media, removable and non-removable media. The system memory 1512 comprises computer readable media in the form of volatile memory, such as random access memory (RAM), and/or non-volatile memory, such as read only memory (ROM). The system memory 1512 typically contains data such as image analysis data 1507 and/or program modules such as operating system 1505 and image analysis software 1506 that are immediately accessible to and/or are presently operated on by the processing unit 1503.

In another aspect, the computer 1501 can also comprise other removable/non-removable, volatile/non-volatile computer storage media. By way of example, FIG. 15 illustrates a mass storage device 1504 which can provide non-volatile storage of computer code, computer readable instructions, data structures, program modules, and other data for the computer 1501. For example and not meant to be limiting, a mass storage device 1504 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 1504, including by way of example, an operating system 1505 and image analysis software 1506. Each of the operating system 1505 and image analysis software 1506 (or some combination thereof) can comprise elements of the programming and the image analysis software 1506. Image analysis data 1507 can also be stored on the mass storage device 1504. Image analysis data 1507 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 1501 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the processing unit 1503 via a human machine interface 1502 that is coupled to the system bus 1513, but can be connected by other interface and bus structures, such as a parallel port, game port, an IEEE 1394 Port (also known as a Firewire port), a serial port, or a universal serial bus (USB).

In yet another aspect, a display device 1511 can also be connected to the system bus 1513 via an interface, such as a display adapter 1509. It is contemplated that the computer 1501 can have more than one display adapter 1509 and the computer 1501 can have more than one display device 1511. For example, a display device can be a monitor, an LCD (Liquid Crystal Display), or a projector. In addition to the display device 1511, other output peripheral devices can comprise components such as speakers (not shown) and a printer (not shown) which can be connected to the computer 1501 via Input/Output Interface 1510. Any step and/or result of the methods can be output in any form to an output device. Such output can be any form of visual representation, including, but not limited to, textual, graphical, animation, audio, tactile, and the like.

The computer 1501 can operate in a networked environment using logical connections to one or more remote computing devices 1514*a,b,c*. By way of example, a remote computing device can be a personal computer, portable computer, a server, a router, a network computer, a peer device or other common network node, and so on. Logical connections between the computer 1501 and a remote computing device 1514*a,b,c* can be made via a local area network (LAN) and a general wide area network (WAN). Such network connections can be through a network adapter 1508. A network adapter 1508 can be implemented in both wired and wireless environments. Such networking environments are conventional and commonplace in offices, enterprise-wide computer networks, intranets, and the Internet. Any type of network 1515 can be used.

For purposes of illustration, application programs and other executable program components such as the operating system 1505 are illustrated herein as discrete blocks, although it is recognized that such programs and components reside at various times in different storage components of the computing device 1501, and are executed by the data processor(s) of the computer. An implementation of image analysis software 1506 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

The invention claimed is:

1. A method for automatic determination of arteriovenous ratio (AVR) in tissue, comprising:
receiving an image;
determining a region of interest (ROI) in the image, wherein the ROI comprises a plurality of centerline pixels;
determining, by a trained classifier, for each of the plurality of centerline pixels within the ROI, a label indicative of the centerline pixel comprising either an artery or a vein;
identifying, based on a voting procedure and the label for each of the plurality of centerline pixels, arteries and veins in the ROI, the ROI having a given diameter, wherein the voting procedure is repeated for ROIs at a plurality of different diameters comprising the given diameter, and wherein the voting procedure votes each centerline pixel as an artery or a vein;
determining vessel width measurements for the identified arteries and veins in the ROI; and
estimating, based on the vessel width measurements for the identified arteries and veins in the ROI, the AVR.

2. The method of claim 1, wherein identifying arteries and veins in the ROI comprises performing vessel segmentation on the image.

3. The method of claim 2, wherein performing vessel segmentation on the image further comprises utilizing the trained classifier to classify vessel pixels or vessel segments in the image.

4. The method of claim 3, wherein vessel tree analysis is used to classify the vessel pixels or vessel segments.

5. The method of claim 3, wherein blood flow is used to classify the vessel pixels or vessel segments.

6. The method of claim 1, wherein decreased AVR indicates higher propensity for a disease.

7. The method of claim 1, wherein the image is one or more of a color image, a multispectral image, or an Optical Coherence Tomography image.

8. The method of claim 1, wherein the image depicts at least one of: a retina, an iris, skin, a brain surface, or a portion of tissue with visible blood vessels.

9. The method of claim 1, wherein determining vessel width measurements for the identified arteries and veins comprises using one or more of a graph search, a multiscale pixel feature based tobogganing method and splats, or profile fitting.

10. The method of claim 9, wherein the graph search uses a multiscale cost function derived from a combination of wavelet kernel lifting.

11. The method of claim 1, wherein the ROI is encapsulated by two concentric circles having diameters derived from a diameter of an optic disc.

12. A system for automatic determination of arteriovenous ratio (AVR), comprising:
memory comprising instructions encoded thereon; and
one or more processors that, when executing the instructions, are caused to perform operations comprising:
receiving an image;
determining a region of interest (ROI) in the image, wherein the ROI comprises a plurality of centerline pixels;
determining, by a trained classifier each of the plurality of centerline pixels within the ROI, a label indicative of the centerline pixel comprising either an artery or a vein;
identifying, based on a voting procedure and the label for each of the plurality of centerline pixels, arteries and veins in the ROI, the ROI having a given diameter, wherein the voting procedure is repeated for ROIs at a plurality of different diameters comprising the given diameter, and wherein the voting procedure votes each centerline pixel as an artery or a vein;
determining vessel width measurements for the identified arteries and veins in the ROI; and
estimating, based on the vessel width measurements for the identified arteries and veins in the ROI, the AVR.

13. The system of claim 12, wherein identifying arteries and veins in the ROI comprises performing vessel segmentation on the image.

14. The system of claim 13, wherein performing vessel segmentation on the image further comprises utilizing the trained classifier to classify vessel pixels or vessel segments in the image.

15. The system of claim 14, wherein vessel tree analysis is used to classify the vessel pixels or vessel segments.

16. The system of claim 14, wherein blood flow is used to classify the vessel pixels or vessel segments.

17. The system of claim 12, wherein decreased AVR indicates higher propensity for a disease.

18. The system of claim 12, wherein the image is one or more of a color image, a multispectral image, or an Optical Coherence Tomography image.

19. The system of claim 12, wherein the image depicts at least one of: a retina, an iris, skin, a brain surface, or a portion of tissue with visible blood vessels.

20. A non-transitory computer-readable medium comprising processor-executable instructions for automatic determination of arteriovenous ratio (AVR) in tissue that, when executed by at least one processor of a computing device, cause the computing device to:
receive an image;
determine a region of interest (ROI) in the image, wherein the ROI comprises a plurality of centerline pixels;
determine, by a trained classifier each of the plurality of centerline pixels within the ROI, a label indicative of the centerline pixel comprising either an artery or a vein;
identify, based on a voting procedure and the label for each of the plurality of centerline pixels, arteries and veins in the ROI, the ROI having a given diameter, wherein the voting procedure is repeated for ROIs at a plurality of different diameters comprising the given diameter, and wherein the voting procedure votes each centerline pixel as an artery or a vein;
determine vessel width measurements for the identified arteries and veins in the ROI; and
estimate, based on the vessel width measurements for the identified arteries and veins in the ROI, the AVR.

* * * * *